US012603183B2

(12) United States Patent
Kakkar et al.

(10) Patent No.: US 12,603,183 B2
(45) Date of Patent: Apr. 14, 2026

(54) SYSTEMS AND METHODS FOR A DYNAMIC SCHEDULING OF APPOINTMENTS BASED ON REAL-TIME HEALTH CONDITIONS OF USERS

(71) Applicant: Optum, Inc., Minnetonka, MN (US)

(72) Inventors: Saloni Kakkar, Delhi (IN); Surajit Das, Noida (IN); Gregory J. Boss, Saginaw, MI (US); Lo Fu Tan, Henderson, NV (US)

(73) Assignee: Optum, Inc., Minnetonka, MN (US)

( * ) Notice: Subject to any disclaimer, the term of this patent is extended or adjusted under 35 U.S.C. 154(b) by 258 days.

(21) Appl. No.: 18/045,116

(22) Filed: Oct. 7, 2022

(65) Prior Publication Data

US 2024/0120104 A1     Apr. 11, 2024

(51) Int. Cl.
*G16H 50/30* (2018.01)
*G16H 10/60* (2018.01)
*G16H 80/00* (2018.01)

(52) U.S. Cl.
CPC ............. *G16H 50/30* (2018.01); *G16H 10/60* (2018.01); *G16H 80/00* (2018.01)

(58) Field of Classification Search
CPC ................................ G16H 50/30; G16H 80/00
See application file for complete search history.

(56) References Cited

U.S. PATENT DOCUMENTS

| | | | |
|---|---|---|---|
| 2004/0059599 A1 | 3/2004 | McIvor | |
| 2011/0190595 A1* | 8/2011 | Bennett | A61B 1/05 600/300 |
| 2014/0052463 A1* | 2/2014 | Cashman | G16H 40/20 705/2 |
| 2014/0257852 A1 | 9/2014 | Walker et al. | |
| 2014/0303988 A1 | 10/2014 | Maneri et al. | |
| 2017/0262604 A1 | 9/2017 | Francois | |
| 2018/0144101 A1* | 5/2018 | Bitran | G16H 50/20 |

FOREIGN PATENT DOCUMENTS

DE     102022203454 A1 * 10/2023

* cited by examiner

*Primary Examiner* — Reginald R Reyes
(74) *Attorney, Agent, or Firm* — Bookoff McAndrews, PLLC

(57)     ABSTRACT

Systems and methods are disclosed for scheduling appointments based on changing health conditions of users. The method includes inputting the initial health dataset of a user to a machine learning model configured to identify other users with similar health profiles. A frequency of monitoring, a frequency of appointments, a duration between the appointments, or a type and length of the appointments is determined to generate a schedule of appointments. A subsequent health dataset of the user is received, and health scores, rule scores, or medication scores for the user are determined based on the subsequent health dataset. A plurality of risk scores for the user is evaluated based on the health scores, rule scores, or medication scores. A recent risk score is determined based on a change in the plurality of risk scores. The schedule of appointments is adjusted based on the recent risk score and the user is notified.

17 Claims, 13 Drawing Sheets

SCHEDULING PLATFORM 111

DATA COLLECTION MODULE 201

DATA PROCESSING MODULE 203

COMPUTATION MODULE 205

MONITORING MODULE 207

TRAINING MODULE 209

MACHINE LEARNING MODULE 211

APPOINTMENT MODULE 213

USER INTERFACE MODULE 215

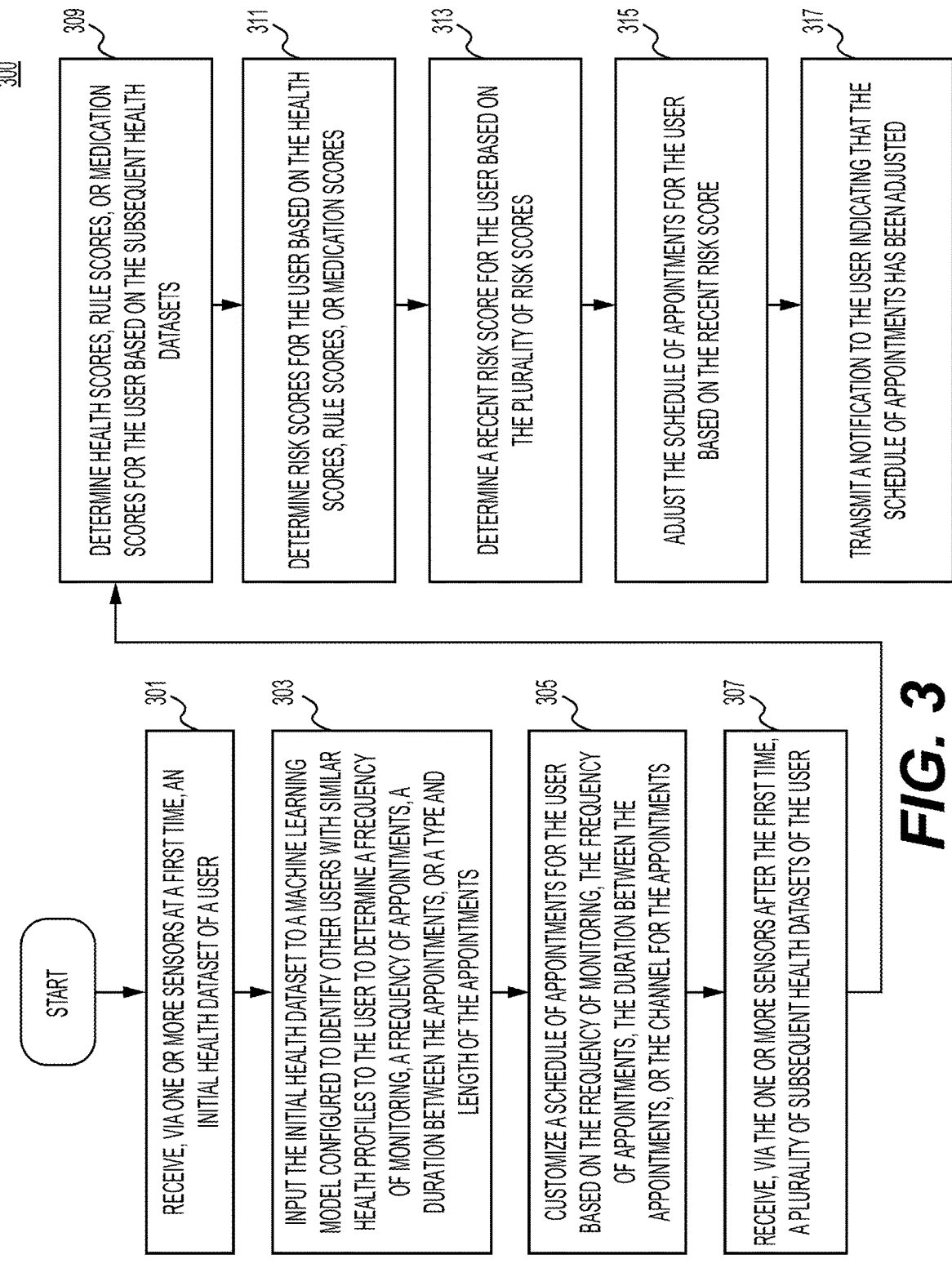

START

301 — RECEIVE, VIA ONE OR MORE SENSORS AT A FIRST TIME, AN INITIAL HEALTH DATASET OF A USER

303 — INPUT THE INITIAL HEALTH DATASET TO A MACHINE LEARNING MODEL CONFIGURED TO IDENTIFY OTHER USERS WITH SIMILAR HEALTH PROFILES TO THE USER TO DETERMINE A FREQUENCY OF MONITORING, A FREQUENCY OF APPOINTMENTS, A DURATION BETWEEN THE APPOINTMENTS, OR A TYPE AND LENGTH OF THE APPOINTMENTS

305 — CUSTOMIZE A SCHEDULE OF APPOINTMENTS FOR THE USER BASED ON THE FREQUENCY OF MONITORING, THE FREQUENCY OF APPOINTMENTS, THE DURATION BETWEEN THE APPOINTMENTS, OR THE CHANNEL FOR THE APPOINTMENTS

307 — RECEIVE, VIA THE ONE OR MORE SENSORS AFTER THE FIRST TIME, A PLURALITY OF SUBSEQUENT HEALTH DATASETS OF THE USER

309 — DETERMINE HEALTH SCORES, RULE SCORES, OR MEDICATION SCORES FOR THE USER BASED ON THE SUBSEQUENT HEALTH DATASETS

311 — DETERMINE RISK SCORES FOR THE USER BASED ON THE HEALTH SCORES, RULE SCORES, OR MEDICATION SCORES

313 — DETERMINE A RECENT RISK SCORE FOR THE USER BASED ON THE PLURALITY OF RISK SCORES

315 — ADJUST THE SCHEDULE OF APPOINTMENTS FOR THE USER BASED ON THE RECENT RISK SCORE

317 — TRANSMIT A NOTIFICATION TO THE USER INDICATING THAT THE SCHEDULE OF APPOINTMENTS HAS BEEN ADJUSTED

701

| DAY | SCORE |
|-----|-------|
| DAY T-5 | 0.33 |
| DAY T-4 | 0.31 |
| DAY T-3 | 0.28 |
| DAY T-2 | 0.20 |
| DAY T-1 | 0.10 |

PATIENT SCORE IN LAST 5 DAYS

703

705

| DAY | SCORE |
|---|---|
| DAY T-5 | 0.02 |
| DAY T-4 | 0.50 |
| DAY T-3 | 0.55 |
| DAY T-2 | 0.30 |
| DAY T-1 | 0.42 |

PATIENT SCORE IN LAST 5 DAYS

707

709

| PATIENT NAME | RECENT RISK SCORE (INC) | DAYS TILL NEXT APPT |
|---|---|---|
| USER A | 0.81 | 15 |
| USER B | 0.79 | 15 |
| USER C | 0.65 | 25 |
| USER D | 0.54 | 21 |
| USER E | 0.52 | 30 |
| USER F | 0.44 | 27 |
| USER G | 0.41 | 10 |

**THIS WILL CONTAIN PATIENTS WITHIN A RANGE OF [X:Y]<-DECIDED BY PROVIDER, AND WITH APPOINTMENTS FAR FROM TODAY

711

| PATIENT NAME | RECENT RISK SCORE (DEC) | DAYS TILL NEXT APPT |
|---|---|---|
| | EMPTY CALENDAR SLOT AVAILABLE | 3 |
| USER H | 0.089 | 2 |
| USER I | 0 | 3 |
| USER J | 0.014 | 3 |
| USER K | 0.034 | 5 |
| USER L | 0.065 | 5 |
| NO SWAP AVAILABLE (FORWARD TO ANOTHER PROVIDER) | | |

*THIS WILL CONTAIN PATIENTS WITHIN A RANGE OF [X:Y]<-DECIDED BY PROVIDER, AND WITH APPOINTMENTS SCHEDULED VERY CLOSE

FIG. 7C

SYSTEMS AND METHODS FOR A DYNAMIC SCHEDULING OF APPOINTMENTS BASED ON REAL-TIME HEALTH CONDITIONS OF USERS

TECHNICAL FIELD

The present disclosure relates generally to a medical scheduling system, and more particularly, to systems and methods for training a machine learning model to dynamically schedule health appointments based on changing health patterns of users.

BACKGROUND

Typically, scheduling health appointments are performed manually on a patient-by-patient basis. For example, a patient visits a physician, and the physician schedules the next appointment based on the assessment of the patient's health condition at the time of the appointment. However, the patient's health condition may change frequently between visits, e.g., the deteriorating health condition of the patient may require an earlier visit to the physician or an improved health condition of the patient may lead to cancellation or postponement of the scheduled appointment to accommodate patients requiring urgent medical attention. However, service providers are technologically challenged to provide a service that monitors, in real-time, the health conditions of the patients, and automatically reschedules health appointments based on the changing health conditions of the patients.

The techniques of this disclosure may solve one or more of the problems set forth above and/or other problems in the art by automatically evaluating, in real-time or near real-time, the health conditions of the users and dynamically rescheduling health appointments based on their changing health conditions. The scope of the current disclosure, however, is defined by the attached claims, and not by the ability to solve any specific problem. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

In one embodiment, a computer-implemented method for scheduling appointments based on changing health conditions of users is disclosed. The computer-implemented method includes: receiving, via one or more sensors at a first time, an initial health dataset of a user, wherein the first time represents a time of an appointment or a time prior to an appointment with a service provider; inputting the initial health dataset to a machine learning model, wherein the machine learning model is configured to identify one or more other users with similar health profiles to the user to determine at least one of a frequency of monitoring, a frequency of appointments, a duration between the appointments, or a type and length of the appointments; customizing a schedule of appointments for the user based on at least one of the frequency of monitoring, the frequency of appointments, the duration between the appointments, or the type and length of the appointments; receiving, via the one or more sensors after the first time, a plurality of subsequent health datasets of the user, wherein the plurality of subsequent health datasets is received at an interval based on the frequency of monitoring; determining at least one of health scores, rule scores, or medication scores for the user based on the subsequent health datasets; determining a plurality of risk scores for the user based on at least one of the health scores, rule scores, or medication scores; determining a recent risk score for the user based on a change in the plurality of risk scores, wherein the recent risk score is indicative of a recent health condition trend of the user; adjusting the schedule of appointments for the user based on the recent risk score; and transmitting a notification to the user indicating that the schedule of appointments has been adjusted.

In accordance with another embodiment, a system for scheduling appointments based on changing health conditions of users is disclosed. The system includes one or more processors, and at least one non-transitory computer readable medium storing instructions which, when executed by the one or more processors, cause the one or more processors to perform operations including: receiving, via one or more sensors at a first time, an initial health dataset of a user, wherein the first time represents a time of an appointment or a time prior to an appointment with a service provider; inputting the initial health dataset to a machine learning model, wherein the machine learning model is configured to identify one or more other users with similar health profiles to the user to determine at least one of a frequency of monitoring, a frequency of appointments, a duration between the appointments, or a type and length of the appointments; customizing a schedule of appointments for the user based on at least one of the frequency of monitoring, the frequency of appointments, the duration between the appointments, or the type and length of the appointments; receiving, via the one or more sensors after the first time, a plurality of subsequent health datasets of the user, wherein the plurality of subsequent health datasets is received at an interval based on the frequency of monitoring; determining at least one of health scores, rule scores, or medication scores for the user based on the subsequent health datasets; determining a plurality of risk scores for the user based on at least one of the health scores, rule scores, or medication scores; determining a recent risk score for the user based on a change in the plurality of risk scores, wherein the recent risk score is indicative of a recent health condition trend of the user; adjusting the schedule of appointments for the user based on the recent risk score; and transmitting a notification to the user indicating that the schedule of appointments has been adjusted.

In accordance with a further embodiment, a non-transitory computer readable medium for scheduling appointments based on changing health conditions of users is disclosed. The non-transitory computer readable medium stores instructions which, when executed by one or more processors, cause the one or more processors to perform operations including: receiving, via one or more sensors at a first time, an initial health dataset of a user, wherein the first time represents a time of an appointment or a time prior to an appointment with a service provider; inputting the initial health dataset to a machine learning model, wherein the machine learning model is configured to identify one or more other users with similar health profiles to the user to determine at least one of a frequency of monitoring, a frequency of appointments, a duration between the appointments, or a type and length of the appointments; customizing a schedule of appointments for the user based on at least one of the frequency of monitoring, the frequency of appointments, the duration between the appointments, or the type and length of the appointments; receiving, via the one or more sensors after the first time, a plurality of subsequent health datasets of the user, wherein the plurality of subsequent health datasets is received at an interval based on the frequency of monitoring; determining at least one of health scores, rule scores, or medication scores for the user based on the subsequent health datasets; determining a plurality of risk scores for the user based on at least one of the health scores, rule scores, or medication scores; determining a recent risk score for the user based on a change in the plurality of risk scores, wherein the recent risk score is indicative of a recent health condition trend of the user; adjusting the schedule of appointments for the user based on the recent risk score; and transmitting a notification to the user indicating that the schedule of appointments has been adjusted.

It is to be understood that both the foregoing general description and the following detailed description are exemplary and explanatory only and are not restrictive of the detailed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 3 is a flowchart of a process for evaluating, in real-time or near real-time, health conditions of patients and scheduling health appointments based on the patients' changing health conditions, according to aspects of the disclosure.

FIG. 7C is a diagram that represents dynamic exchanging of health appointments between patients based on their health scores, according to aspects of the disclosure.

DETAILED DESCRIPTION

Figure 1:
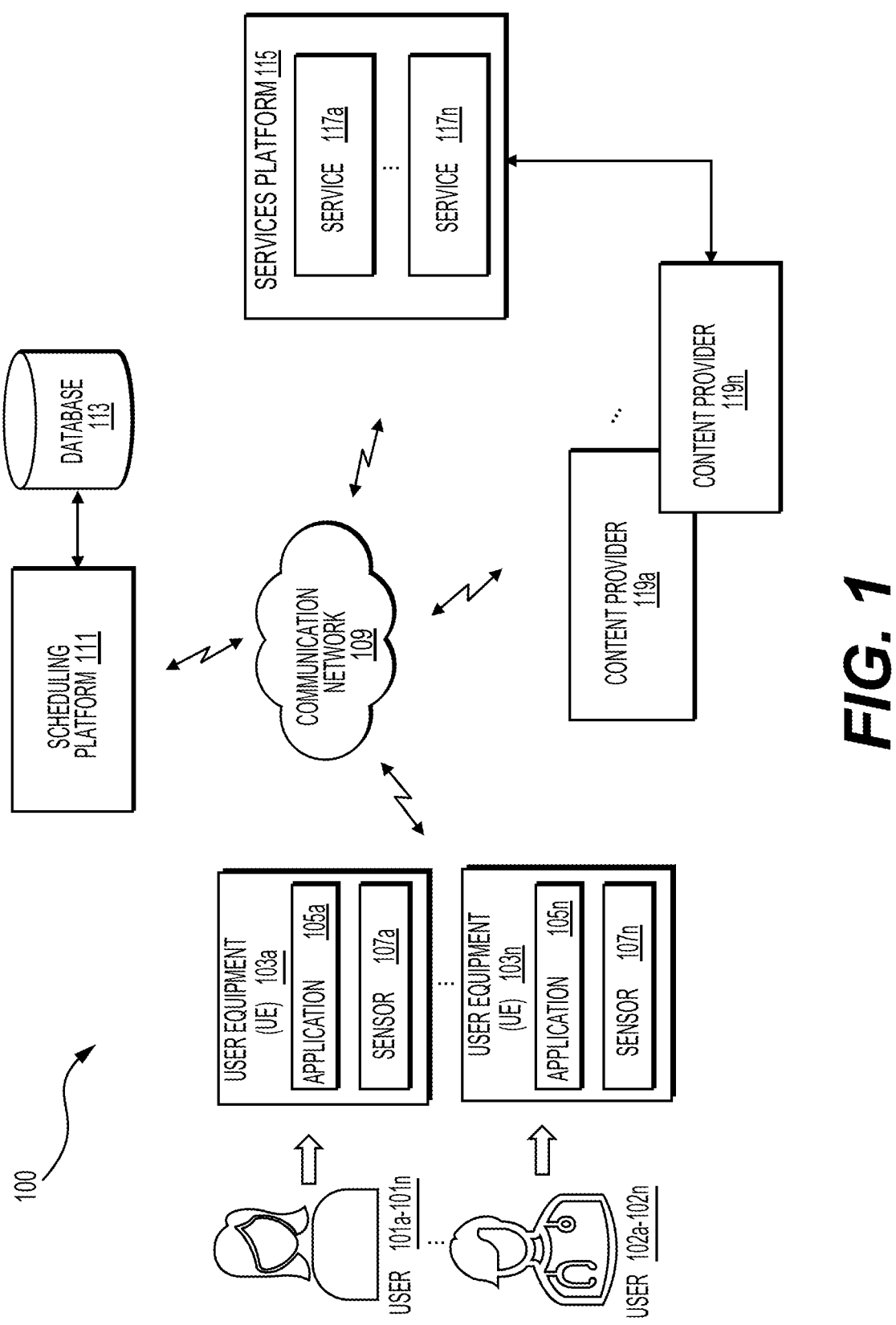
FIG. 1 is a diagram of a system capable of evaluating, in real-time or near real-time, health conditions of patients and scheduling health appointments based on the patients' changing health conditions, according to aspects of the disclosure.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

Various non-limiting embodiments of the present disclosure will now be described to provide an overall understanding of the principles of the structure, function, and use of systems and methods disclosed herein for automatically evaluating, in real-time or near real-time, health conditions of users and dynamically rescheduling appointments based on users' changing health conditions.

Conventionally, scheduling of health appointments is manually handled. Such method is error-prone, time-consuming, and very often inconvenient for the patients, e.g., manual scheduling is limited to office hours. This also limits the existing health system to be reactive, driven solely by inbound patient requests for care.

Health appointments are scheduled based on the assessment of the patient's health condition at the time of the appointment, however, the patient's health condition may change frequently between follow-up appointments. The patients are often on their own to deal with the issues, and such fragmented and intermittent nature of health care is particularly problematic. In one example embodiment, user A visits a physician and is diagnosed with a mental illness. The physician may schedule the next health appointment, e.g., after 1 month, based on the initial assessment and current health condition of user A. However, the health condition of user A may frequently change until the follow-up appointment, sometimes requiring an immediate visit to the physician. Currently, there is no mechanism to monitor, in real-time, the health condition of user A and reschedule the appointments based on the changing health condition. In fact, changing a scheduled appointment may be cumbersome, e.g., the patients may need to contact the service provider and request a different time for the scheduled appointment, which may or may not be available. Also, in many known arrangements, if scheduled appointments are not canceled within a certain time period, a penalty may be levied to the patients, e.g., a cancelation fee. Hence, the patients need to reschedule their appointments within a certain time frame, which is not always possible or practical.

The existing health system does not utilize the ubiquitous modern technological infrastructure to continuously monitor the health conditions of the patients to reschedule their appointments. Rather, the patients need to reschedule their health appointments based on their assessment and needs. The patients may be assisted by healthcare employees while manually rescheduling the appointment. In one example embodiment, patients monitor their vitals/conditions and may report the events that may be clinically significant to the healthcare provider whereupon the healthcare provider may decide to bring in the patients before their scheduled appointment. The current health system is technically challenged to implement a method that: (i) evaluates, in real-time, changing health conditions of the patients, (ii) reschedules, in real-time, appointments of the patients based on the changing health patterns, and (iii) ensure data security for confidential and sensitive patient health data by implementing specific encryption algorithms and data security standards. There is a need for a methods and systems that automatically evaluate a patient's changing health conditions and automatically reassess the timing for the next physician visit.

To address these technical challenges, system 100 of FIG. 1 introduces the capability to automatically evaluate, in real-time or near real-time, health conditions of users (e.g., patients) and dynamically reschedule the users' appointments based on their changing health conditions. System 100 implements evidence-based evaluations to set up an initial appointment for a patient along with a remote patient monitoring capability to dynamically change the scheduled appointment based on an analysis of the patient's changing health conditions. Such dynamic scheduling of appointments reduces the risk of emergency appointments and improves operational efficiency by optimizing the appointment scheduling workflow process.

FIG. 1 introduces a capability to implement modern communication and data processing capabilities into methods and systems for dynamically rescheduling health appointments based on real-time health conditions of users, according to one example embodiment. FIG. 1, an example architecture of one or more example embodiments of the present invention, includes system 100 that comprises user 101a-101n (collectively referred to as user 101), user 102a-102n (collectively referred to as user 102), user equipment (UE) 103a-103n (collectively referred to as UE 103) that includes application 105a-105n (collectively referred to as application 105) and sensors 107a-107n (collectively referred to as sensor 107), communication network 109, scheduling platform 111, database 113, services platform 115 that includes service 117a-117n (collectively referred to as service 117), and content providers 119a-119n (collectively referred to as content provider 119).

In one embodiment, user 101 may be a person or a group of people interacting with a user interface or a web interface of UE 103 to access a service, e.g., a scheduling service. In one example embodiment, user 101 may include a registered patient, a potential patient, a returning patient, a visiting patient, an authorized user, etc., that provide contextual information, e.g., health-related information, personal information, etc., to access the service. In one embodiment, user 101 may opt-in to share their health-related information, e.g., blood pressure, body temperature, skin temperature, heart rate variability, heart rate, resting heart rate, breathing rate, blood glucose, oxygen saturation, stress levels, etc. In another embodiment, user 101 may share specialized health indicators, e.g., lab data, blood indicators, physiological data, weight data, etc. In a further embodiment, user 101 may share medication charts, schedule information, medical intake information, calendar appointments, location information, preference information, e.g., specific people as caretakers, healthcare insurance benefit details, etc. Such individualized patient information pertaining to preferences may result in refined scheduling of appointments with better quality, outcomes, and improved patient experience and satisfaction.

In one embodiment, user 102 may be a service provider, e.g., physicians, nurses, healthcare professionals, medical staff, etc., that provides medical records, medical history, family/hereditary history, appointment information, or a combination thereof associated with one or more patients. In one embodiment, user 102, via system 100, may whitelist one or more patients who require continuous monitoring or ongoing appointments. In another embodiment, user 102 may opt-in to share: (i) appointment scheduler, (ii) current scheduling program access, (iii) patients' files, documents, information, medical history, medication, family/hereditary health history, and/or other health parameters at the time of the appointment. In another embodiment, user 102 may provide a set of rules or specialized health indicators to be monitored at a given time interval. User 102 may also tag other service providers as trusted providers, in case of unavailability for critical care or urgent patient need. User 102 may also opt-in to share past appointment details, health parameters or diagnosis of the patients, and/or clinical data of the patients with the system for enhancements.

In one embodiment, UE 103 may include, but is not restricted to, any type of a mobile terminal, wireless terminal, fixed terminal, or portable terminal. Examples of the UE 103, may include, but are not restricted to, a mobile handset, a wireless communication device, a station, a unit, a device, a multimedia computer, a multimedia tablet, an Internet node, a communicator, a desktop computer, a laptop computer, a notebook computer, a netbook computer, a tablet computer, a Personal Communication System (PCS) device, a personal navigation device, a Personal Digital Assistant (PDA), a digital camera/camcorder, an infotainment system, a dashboard computer, a television device, or any combination thereof, including the accessories and peripherals of these devices, or any combination thereof. In addition, the UE 103 may facilitate various input means for receiving and generating information, including, but not restricted to, a touch screen capability, a keyboard, and keypad data entry, a voice-based input mechanism, and the like. Any known and future implementations of the UE 103 may also be applicable.

In one embodiment, applications 105 may include various applications such as, but not restricted to, scheduling applications, content provisioning applications, networking applications, multimedia applications, media player applications, camera/imaging applications, software applications, and the like. In one embodiment, one of the applications 105 at UE 103 may act as a client for scheduling platform 111 and may perform one or more functions associated with the functions of scheduling platform 111 by interacting with scheduling platform 111 over communication network 109.

By way of example, sensor 107 may be any type of sensor. In one embodiment, sensors 107 may include, for example, sensors capable of capturing the user's health data (e.g., activity data, vitals data, and any other data that may be indicative of the user's health condition), e.g., inertial measurement unit (IMU) sensors, electrocardiogram (ECG) sensors, sensors to detect blood glucose level, sensors to measure respiration rate, heart rate detection sensors, sensor to monitor body temperature, micro-electro-mechanical system (MEMS) based miniature motion sensors, gyroscope, accelerometer, magnetometer, infrared sensor, camera, microphone, gas sensor, photo-detector, etc. In another embodiment, sensors 107 may include, for example, a network detection sensor for detecting wireless signals or receivers for different short-range communications (e.g., Bluetooth, Wi-Fi, Li-Fi, near field communication (NFC), etc.), a global positioning sensor for gathering location data, a camera/imaging sensor for gathering image data, an audio recorder for gathering audio data, and the like. In one example embodiment, sensors 107 may be provided in the wearable device and/or a health monitoring device, which may capture parameters such as eating/drinking pattern, exercise regime, medication intake, age, weight, gender, etc., of user 101. In another example embodiment, the camera/imaging sensor may be either a monocular or a stereo camera that captures 3D data of the user's body, e.g., capture a sequence of images or videos of user 101 taking medication prescribed by the physician.

In one embodiment, various elements of system 100 may communicate with each other through communication network 109. Communication network 109 may support a variety of different communication protocols and communication techniques. In one embodiment, communication network 109 allows scheduling platform 111 to communicate with UE 103, service platform 115, and content provider 119. The communication network 109 of system 100 includes one or more networks such as a data network, a wireless network, a telephony network, or any combination thereof. It is contemplated that the data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network may be, for example, a cellular communication network and may employ various technologies including 5G (5th Generation), 4G, 3G, 2G, Long Term Evolution (LTE), wireless fidelity (Wi-Fi), Bluetooth®, Internet Protocol (IP) data casting, satellite, mobile ad-hoc network (MANET), vehicle controller area network (CAN bus), and the like, or any combination thereof.

In one embodiment, scheduling platform 111 may be a platform with multiple interconnected components. Scheduling platform 111 may include one or more servers, intelligent networking devices, computing devices, components, and corresponding software for evaluating, in real-time, the health conditions of the users and dynamically rescheduling appointments based on their changing health conditions. In addition, it is noted that scheduling platform 111 may be a separate entity of system 100. Further details of scheduling platform 111 are provided below.

In one embodiment, database 113 may be any type of database, such as relational, hierarchical, object-oriented, and/or the like, wherein data are organized in any suitable manner, including as data tables or lookup tables. In one embodiment, database 113 may store and manage multiple types of information that can provide means for aiding in the content provisioning and sharing process. In an embodiment, database 113 may include a machine-learning based training database with pre-defined mapping defining a relationship between various input parameters and output parameters based on various statistical methods. In an embodiment, the training database may include machine-learning algorithms to learn mappings between input parameters related to the user such as but not limited to physiological parameters, user's health records, user's lifestyle pattern, etc., and inputs provided by the experts. In an embodiment, the training database may include a dataset that may include data collections that are not subject-specific, e.g., data collections based on population-wide observations, local, regional or super-regional observations, and the like. Exemplary datasets include environmental information, drug interaction information, geographic data, climate data, meteorological data, retail data, pharmacy data, insurance data, market data, encyclopedias, scientific and medical-related periodicals and journals, business information, research studies data, scientifically-curated genetics-related information, nutritional data, exercise data, physician and hospital/clinic location information, physician billing information, physician reimbursement information, and the like. In an embodiment, the training database is routinely updated and/or supplemented based on machine learning methods.

The services platform 115 may include any type of service. By way of example, services platform 115 may include scheduling services, social networking services, content (e.g., audio, video, images, etc.) provisioning services, application services, storage services, contextual information determination services, location-based services, notification services, information (e.g., weather, news, etc.) based services, etc. In one embodiment, the services platform 115 may interact with UE 103, scheduling platform 111, and content provider 119 to supplement or aid in the processing of the content information. In one embodiment, services platform 115 may be implemented or embedded in scheduling platform 111 or in its functions. In one example embodiment, services platform 115 may allow scheduling platform 111 access to user account information from social networks and to retrieve social network activity data from the social networks.

By way of example, services 117 may be an online service that reflects the interests and/or activities of user 101. The services 117 may share user profile information, activity information, contextual information, historical user information and interests, and/or location information within their individual networks, and provides for data portability. In one example embodiment, services 117 may assist in providing scheduling platform 111 with health-related information, e.g., activity information that may affect the health conditions of the users, contextual information that may affect the scheduled appointment for the users, and a variety of additional information.

In one embodiment, content provider 119 may provide content to UE 103, scheduling platform 111, and services 117 of services platform 115. The content provided may be any type of content, such as image content (e.g., pictures), textual content, audio content, video content, etc. In one embodiment, content provider 119 may provide content that may supplement the content of applications 105, sensors 107, or a combination thereof. In one embodiment, content provider 119 may also store content associated with UE 103, scheduling platform 111, and services 117 of the services platform 115. In another embodiment, content provider 119 may manage access to a central repository of data and offer a consistent, standard interface to data.

By way of example, UE 103, scheduling platform 111, services platform 115, and content provider 119 may communicate with each other and other components of the communication network 109 using well known, new or still developing protocols. In this context, a protocol includes a set of rules defining how the network nodes within the communication network 109 interact with each other based on information sent over the communication links. The protocols are effective at different layers of operation within each node, from generating and receiving physical signals of various types, to selecting a link for transferring those signals, to the format of information indicated by those signals, to identifying which software application executing on a computer system sends or receives the information. The conceptually different layers of protocols for exchanging information over a network are described in the Open Systems Interconnection (OSI) Reference Model.

Communications between the network nodes are typically effected by exchanging discrete packets of data. Each packet typically comprises (1) header information associated with a particular protocol, and (2) payload information that follows the header information and contains information that may be processed independently of that particular protocol. In some protocols, the packet includes (3) trailer information following the payload and indicating the end of the payload information. The header includes information such as the source of the packet, its destination, the length of the payload, and other properties used by the protocol. Often, the data in the payload for the particular protocol includes a header and payload for a different protocol associated with a different, higher layer of the OSI Reference Model. The header for a particular protocol typically indicates a type for the next protocol contained in its payload. The higher layer protocol is said to be encapsulated in the lower layer protocol. The headers included in a packet traversing multiple heterogeneous networks, such as the Internet, typically include a physical (layer 1) header, a data-link (layer 2) header, an internetwork (layer 3) header and a transport (layer 4) header, and various application (layer 5, layer 6 and layer 7) headers as defined by the OSI Reference Model.

Figure 2:
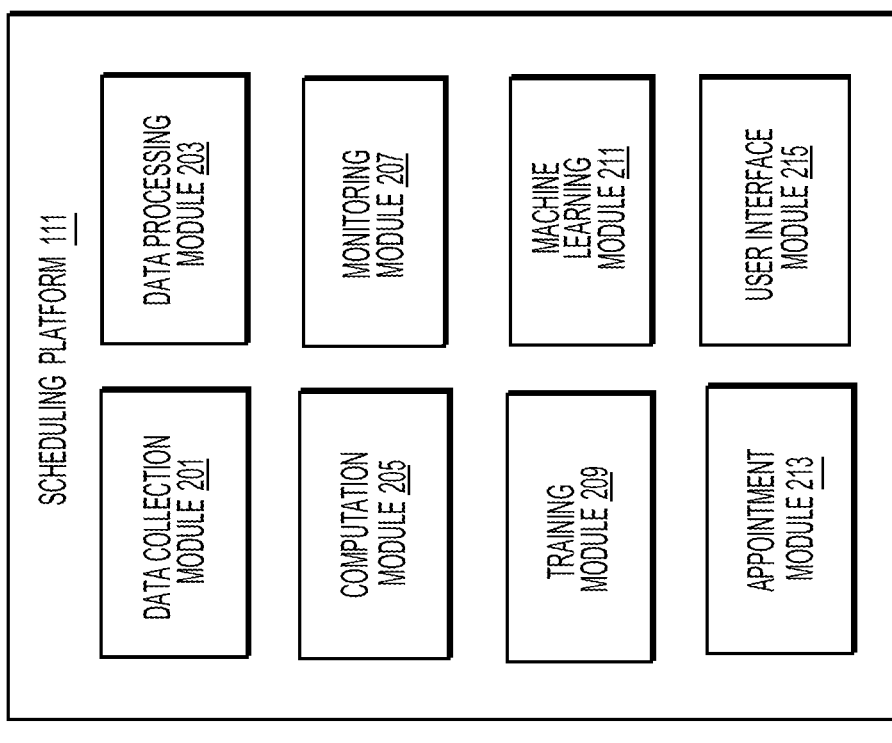
FIG. 2 is a diagram of the components of scheduling platform 111, according to aspects of the disclosure.

FIG. 2 is a diagram of the components of scheduling platform 111, according to one example embodiment. As used herein, terms such as "component" or "module" generally encompass hardware and/or software, e.g., that a processor or the like may use to implement associated functionality. By way of example, scheduling platform 111 includes one or more components for automatically evaluating, in real-time or near real-time, health conditions of users and dynamically rescheduling health appointments based on the users' changing health conditions. It is contemplated that the functions of these components may be combined in one or more components or performed by other components of equivalent functionality. In one embodiment, scheduling platform 111 comprises data collection module 201, data processing module 203, computation module 205, monitoring module 207, training module 209, machine learning module 211, appointment module 213, user interface module 215, or any combination thereof.

In one embodiment, data collection module 201 may collect relevant data, e.g., health data, health appointment data, behavioral data, contextual data, etc., associated with user 101 through various data collection techniques. The data collection module 201 may use a web-crawling component to access various databases, e.g., database 113, or other information sources, e.g., content provider 119, to collect relevant data associated with user 101. In one example embodiment, data collection module 201 may collect health data associated with user 101 via a variety of UE 103, e.g., monitoring devices that measures the physiological parameters, e.g., heart rate, blood oxygen saturation levels, respiratory rate, glucose level, blood pressure, weight, etc., of user 101. In another example embodiment, UE 103 may include a smartwatch, a smart wristband, a smartphone, smart clothing, or other devices including sensors 107, e.g., a gyroscope, an accelerometer, a magnetometer, an infrared sensor, a camera, a microphone, a gas sensor, a photo-detector, etc., capable of capturing activity data and vital data of user 101. In one embodiment, these monitoring devices may be equipped with operating systems like Android™, (OS™, Windows®, Linux™ OS, or hybrid frameworks that enable efficient integration. In one embodiment, the collection of relevant data may be automated, e.g., an automatic human activity recognition technique that captures data from wearable and/or non-wearable monitoring devices. The human activity recognition technique may be used to build Human Activity Recognition (HAR) datasets. In one embodiment, data collection module 201 may include various software applications, e.g., data mining applications in Extended Meta Language (XML), that automatically search for and return relevant data regarding user 101. In one embodiment, data collection module 201 may parse and arrange the data into a common format that can be easily processed by other modules and platforms. In another embodiment, data collection module 201 may collect, e.g., in real-time or near real-time, videos or one or more images of user 101 from sensor 107, e.g., image sensors, cameras, etc., to collect user activity information, e.g., medication intake, exercises, etc., biometric data, e.g., fingerprints, facial images, etc.

In one embodiment, data processing module 203 may process data collected by data collection module 201. In one embodiment, data processing module 203 may process activity data of user 101 to determine their lifestyle patterns, e.g., eating patterns, drinking patterns, sleeping patterns, exercise patterns, and other activities data such as smoking, drinking, etc. In another embodiment, data processing module 203 may process health-related data of user 101, e.g., blood pressure, body temperature, skin temperature, heart rate variability, heart rate, resting heart rate, breathing rate, blood glucose, oxygen saturation, or stress levels, to determine changing health conditions. In a further embodiment, data processing module 203 may process calendar information of user 101, e.g., patients, and user 102, e.g., physicians, to determine availability information and potential conflicts in appointments. In another embodiment, data processing module 203 may process one or more images/videos to determine medication adherence by user 101.

In one embodiment, computation module 205 may receive the processed data from data processing module 203 and may perform various calculations on the processed data to determine health scores, rule scores, or medication scores of user 101. In one example embodiment, computation module 205 may calculate health scores based, at least in part, on the health parameters of user 101 (e.g., patient). The health parameters of user 101 may include blood pressure, body temperature, skin temperature, heart rate variability, heart rate, resting heart rate, breathing rate, blood glucose levels, oxygen saturation levels, stress levels, or a combination thereof. In another example embodiment, computation module 205 may calculate rule scores based, at least in part, on adherence to a customized rule set by user 101. The customized rule set may include physical activities for a predetermined time period, a body mass index (BMI) range, a prescribed diet, laboratory test values, or a combination thereof, and may be set by user 102 (e.g., health care provider). In a further example embodiment, computation module 205 may calculate medication scores based, at least in part, on adherence to prescribed medication by user 101. In another embodiment, computation module 205 may generate risk scores of user 101 by performing various calculations on the health scores, rule scores, and medication scores. In one example embodiment, computation module 205 may calculate risk scores by adding the health scores, rule scores, and medication scores. It is understood that any other means of calculations may be performed on the health scores, rule scores, and medication scores to generate risk scores. In one example embodiment, computation module 205 may determine a recent risk score that indicate the recent health condition trend for user 101 based, at least in part, on the plurality of risk scores, historical information, or a combination thereof.

In one embodiment, monitoring module 207 may compare, in real-time or near real-time, the health scores to a pre-determined health score threshold. In one example embodiment, monitoring module 207 may determine the health score to be perfect, e.g., 0, when all the health parameters are within the pre-determined health score threshold, e.g., baseline parameters. Monitoring module 207 may determine the health scores on upper limits of the pre-determined health score threshold to indicate critical risk to health, and such deviations may be marked at 1. As the deviations approach the upper limits, the health scores start approaching 1. In another embodiment, monitoring module 207 may compare, in real-time or near real-time, the rule scores to a pre-determined rule score threshold. In one example embodiment, monitoring module 207 may determine the rule score to be perfect, e.g., 0, when all the specialized health indicators are within the pre-determined rule score threshold, e.g., baseline parameters. Monitoring module 207 may determine the rule scores on upper limits of the pre-determined rule score threshold to indicate critical risk to health, and such deviations may be marked at 1. As the deviations approach the upper limits, the rule scores start approaching 1. In a further embodiment, monitoring module 207 may compare, in real-time or near real-time, the medication scores to a pre-determined medication score threshold. In one example embodiment, monitoring module 207 may determine the medication score to be perfect, e.g., 0, when medication adherence is within the pre-determined medication score threshold, i.e., all medication is adhered to by user 101. Monitoring module 207 may determine the medication scores on upper limits of the pre-determined medication score threshold to indicate critical risk to health, and such deviations may be marked at 1. As the deviations approach the upper limits, the medication scores start approaching 1. In another embodiment, monitoring module 207 may compare, in real-time or near real-time, the risk score to a pre-determined risk score threshold. In one example embodiment, monitoring module 207 may determine the risk score to be low, moderate, high, severe, or critical based on the comparison.

In one embodiment, training module 209 may provide learning, or training, to machine learning module 211 by providing training data, e.g., data from other modules, that contains input and correct output, to allow machine learning module 211 to learn over time. The training may be performed based on the deviation of a processed result from a documented result when the inputs are fed into machine learning module 211, e.g., an algorithm measures its accuracy through the loss function, adjusting until the error has been sufficiently minimized. Training module 209 may conduct the training in any suitable manner, e.g., in batches, and may include any suitable training methodology. Training may be performed periodically, and/or continuously, e.g., in real-time or near real-time. Further details of training a machine learning module are provided below.

In one embodiment, machine learning module 211 may receive the training data from training module 209 to schedule or reschedule health appointments based on changing health conditions of the users. Machine learning module 211 may randomize the ordering of the training data, visualize the training data to identify relevant relationships between different variables, identify any data imbalances, split the training data into two parts where one part is for training a model and the other part is for validating the trained model, de-duplicating, normalizing, correcting errors in the training data, and so on. Machine learning module 211 may implement various machine learning techniques, e.g., k-nearest neighbors, cox proportional hazards model, decision tree learning, association rule learning, neural network (e.g., recurrent neural networks, convolutional neural networks, deep neural networks), inductive programming logic, support vector machines, Bayesian models, etc. In another embodiment, machine learning module 211 may leverage one or more classification models trained to classify the training data and/or one or more prediction models trained to predict an outcome based on the training data. In one example embodiment, a dynamic scheduler may generate, in real-time, risk score for user 101 for rescheduling an appointment. The dynamic scheduler may also monitor, in real-time, an improvement or a deterioration in the health conditions of user 101 based on the risk scores, for rescheduling the appointment. The dynamic scheduler may also incorporate input from user 101, e.g., consent or refusal to the rescheduled appointments, and the decision of user 102 as true labels while rescheduling the appointment. Such data on the risk scores, health data, and rescheduled appointments may be utilized to build and train a machine learning model, e.g., to predict rescheduling of appointments, automatic rescheduling of appointments, etc. Further details of machine learning module are provided below.

In one embodiment, appointment module 213 may schedule or reschedule, in real-time or near real-time, health appointments for user 101 based on their changing health conditions. In one example embodiment, appointment module 213 may communicate, via communication network 109, any changes in health appointments to a physician or health professionals for confirmation. The appointment module 213 may then communicate the rescheduled appointments to the patients. In another embodiment, appointment module 213 may communicate an appointment reminder to user 101 on a scheduled basis or automated basis to prevent cancellation. The appointment reminder may include travel directions for the appointment, a customized message for the patient, travel time information, etc.

In one embodiment, user interface module 215 may enable a presentation of a graphical user interface (GUI) in UE 103. User interface module 215 may employ various application programming interfaces (APIs) or other function calls corresponding to application 105 on UE 103, thus enabling the display of graphics primitives such as icons, menus, buttons, data entry fields, etc. In another embodiment, user interface module 215 may cause interfacing of guidance information with user 101 to include, at least in part, one or more annotations, audio messages, video messages, or a combination thereof. In one example embodiment, user interface module 215 may comprise a variety of interfaces, for example, interfaces for data input and output devices, referred to as I/O devices, storage devices, and the like. Still further, user interface module 215 may be configured to operate in connection with augmented reality (AR) processing techniques, wherein various applications, graphic elements, and features may interact. In one example embodiment, user interface module 215 may display a booking widget in UE 103, and the booking widget may be linked to websites of various user 102. The user interface module 215 may ensure that the booking widget is distinctive to be recognized by the users and unobtrusive to avoid any negative user experiences while visiting the linked websites. In one example embodiment, scheduling platform 111 may communicate with user 101 regarding the requirement for a change in the appointment and may provide user 101 with details on his health conditions and risk factors. Scheduling platform 111 may also generate various user interface elements in UE 103, e.g., a survey, to receive a response from user 101 regarding rescheduling of the appointment, for example:

Feedback: "Yes, I Feel discomfort in my current line of treatment," "No, I am doing fine."

Confirmation: "Yes, I am okay to move the appointment to the suggested slot."

Cancelation: "No, I am not available in the suggested slot and would prefer to keep my existing appointment."

Shift: "I am not available at the proposed slot and request an alternative slot."

The above presented modules and components of scheduling platform 111 may be implemented in hardware, firmware, software, or a combination thereof. Though depicted as a separate entity in FIG. 2, it is contemplated that scheduling platform 111 may be implemented for direct operation by respective UE 103. As such, scheduling platform 111 may generate direct signal inputs by way of the operating system of the UE 103. In another embodiment, one or more of the modules 201-215 may be implemented for operation by respective UEs, as scheduling platform 111, or a combination thereof. The various executions presented herein contemplate any and all arrangements and models.

Figure 9:
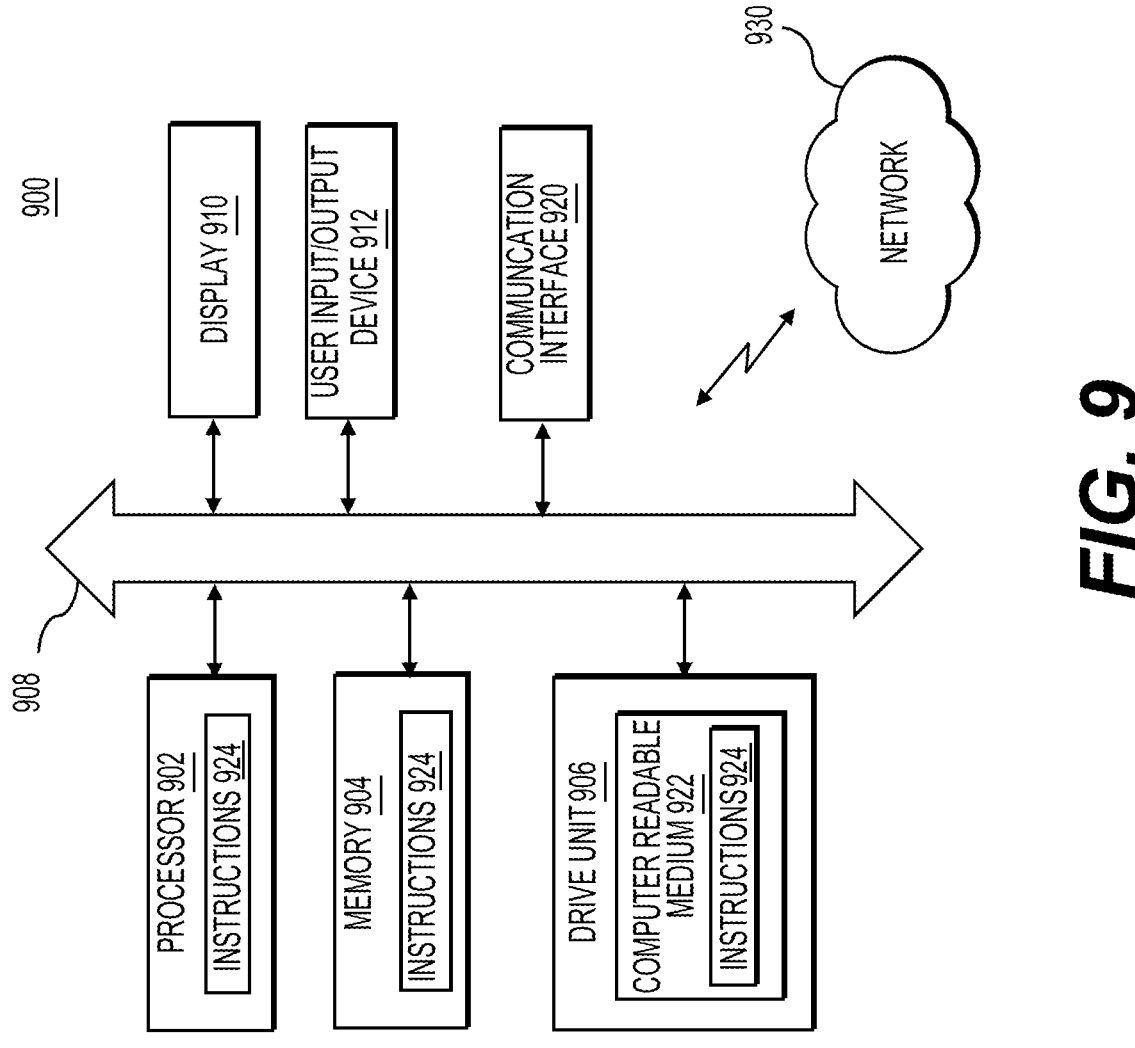
FIG. 9 illustrates an implementation of a general computer system that may execute techniques presented herein.

FIG. 3 is a flowchart of a process for evaluating, in real-time or near real-time, health conditions of users, e.g., patients, and scheduling health appointments based on the users' changing health conditions, according to one example embodiment. In various embodiments, scheduling platform 111 and/or any of modules 201-215 may perform one or more portions of process 300 and may be implemented in, for instance, a chip set including a processor and a memory as shown in FIG. 9. As such, scheduling platform 111 and/or any of modules 201-215 may provide means for accomplishing various parts of process 300, as well as means for accomplishing embodiments of other processes described herein in conjunction with other components of system 100. Although process 300 is illustrated and described as a sequence of steps, it is contemplated that various embodiments of process 300 may be performed in any order or combination and need not include all of the illustrated steps.

In step 301, scheduling platform 111 may receive, via one or more sensors 107 at a first time, an initial health dataset of a user 101 (e.g., patient). In one embodiment, the first time represents a time of an appointment or a time prior to an appointment with a service provider. In one embodiment, the initial health dataset includes health-related data, medical records, clinical data, appointment schedules, location information, preference information, insurance information, access credentials, or a combination thereof.

In step 303, scheduling platform 111 may input the initial health dataset to a machine learning module 211. The machine learning module 211 may apply various machine learning algorithms to identify one or more other users with similar health profiles to user 101 to determine a frequency of monitoring, a frequency of appointments, a duration between the appointments, or a type and length of the appointments. In one embodiment, machine learning module 211 may implement K-nearest neighbors to determine the similarity between the health profiles of user 101 and other patients. For example, scheduling platform 111 may determine user 101 has depression and high blood pressure. Scheduling platform 111, via machine learning module 211, may determine other patients with a similar health condition, i.e., depression and high blood pressure. The machine learning module 211 may process the health profiles of the other patients to determine their frequency of monitoring, frequency of appointments, duration between the appointments, and/or a type and length of the appointments. In some embodiments, scheduling platform 111 may determine the frequency of monitoring, frequency of appointments, duration between the appointments, and/or a type and length of the appointments without any machine learning technique. The machine learning module 211 may calculate from the determined data of the other patients a probability of monitoring, appointments, and/or type and length of the appointments, e.g., telemedicine or in-person visits, for user 101.

In step 305, scheduling platform 111 may customize (or determine) a schedule of appointments for user 101 based on the frequency of monitoring, frequency of appointments, duration between the appointments, and/or type and length of the appointments. In one example embodiment, scheduling platform 111 may schedule a virtual or in-person appointment for user 101 every month with a physician, and user 101 vitals, or any health-related data, may be monitored on a real-time or near real-time basis.

In step 307, scheduling platform 111 may receive, via one or more sensors after the first time, a plurality of subsequent health datasets of the user. In one embodiment, the plurality of subsequent health datasets is received at an interval based on the frequency of monitoring. In one embodiment, the plurality of subsequent health datasets includes health-related data, medical records, clinical data, appointment schedules, location information, preference information, insurance information, access credentials, or a combination thereof.

In step 309, scheduling platform 111 may determine at least one of health scores, rule scores, or medication scores for user 101 based on the subsequent health datasets. In some embodiments, the health score, rule scores, and medication scores for user 101 may be determined based on the subsequent health datasets and the initial health dataset. In one embodiment, scheduling platform 111 may process the plurality of subsequent health datasets to determine the health parameters of user 101. The health parameters may include blood pressure, body temperature, skin temperature, heart rate variability, breathing rate, blood glucose levels, oxygen saturation levels, stress levels, or a combination thereof. Scheduling platform 111 may calculate the health scores based on one or more of the health parameters, with each health parameter weighted accordingly, for example:

$$\text{Health Score}=wh1*\text{Blood\_glucose\_score}+wh2*BP\_\text{score}+wh3*\text{body\_temp\_score}+\ldots$$

The health scores are then compared to a pre-determined health score threshold.

In another embodiment, scheduling platform 111 may receive, via one or more UE 103 associated with user 102 (e.g., healthcare provider), a customized rule set for UE 103. In one embodiment, a customized rule set may include physical activities for a predetermined time period, a body mass index (BMI) range, a prescribed diet, laboratory test values, or a combination thereof, e.g., indicated as X1, X2, X3, X4. Scheduling platform 111 may process the plurality of subsequent health datasets to determine adherence to the customized rule set or a deviation from the customized rule set by user 101. Scheduling platform 111 may calculate the rule scores based on adherence to the customized rule set or the deviation from the customized rule set, with each parameter (e.g., X1, X2, X3, X4, etc.) weighted accordingly, for example:

$$\text{Rule Score}=wr1*X1\_\text{score}+wr2*X2\_\text{score}+wr3*X3\_\text{score}+\ldots$$

The rule scores are then compared to a pre-determined rule score threshold.

In a further embodiment, scheduling platform 111 may receive, via one or more sensors 107, a plurality of images and/or a plurality of video sequences representative of adherence or a deviation by user 101 to a prescribed medication, e.g., indicated as Y1, Y2, Y3. Scheduling platform 111 may process the plurality of images and/or the plurality of video sequences to generate the medication scores for the user, with each parameters (e.g., Y1, Y2, Y3, etc.) weighted accordingly, for example:

$$\text{Medication Score}=wm1*Y1\_\text{score}+wm2*Y2\_\text{score}+wm3*Y3\_\text{Score}+\ldots$$

The medication scores are then compared to a pre-determined medication score threshold.

In step 311, scheduling platform 111 may determine a plurality of risk scores for user 101 based on at least one of the health scores, rule scores, or medication scores. In one embodiment, scheduling platform 111 may calculate the plurality of risk scores by adding the health scores, the rule scores, and the medication scores after the first time, with each type of score weighted accordingly, for example:

$$\text{Risk Score: } W1*\text{Health Score}+W2*\text{Rule Score}+W3*\text{Medication Score}$$

In an example embodiment, the score may lie between 0 and 1 (0 being the lowest risk score and 1 being the highest risk score). Further, scheduling platform 111 may label risks as low, moderate, high, severe, or critical depending on this risk score:

1. 0 to 0.2=>low risk
2. 0.21 to 0.4=>moderate risk
3. 0.41 to 0.6=>high risk
4. 0.61 to 0.8=>severe risk
5. 0.81 to 1=>critical risk It is understood that any other method of calculation may be implemented to calculate the risk scores. In one example embodiment, scheduling platform 111 may gather industry baselines for health and other parameters of user 101 and may evaluate risk scores. Scheduling platform 111 may collect, in real-time or near real-time, health parameters of user 101. The health parameters may include blood pressure, body temperature, skin temperature, heart rate variability, heart rate, resting heart rate, breathing rate, blood glucose, oxygen saturation, stress levels, etc. The health parameters may also include weight, fatigue, and/or weakness via means of surveys, feedback, questionnaires, or notification. The health parameters may further include specialized health indicators and medication intake information. Scheduling platform 111 may process the health parameters to create a regular and stressful threshold, e.g., baseline, for each health parameter. Scheduling platform 111 may compare risk scores to the threshold and identify any deviations in the metrics, activities that may affect the metrics, e.g., walking, exercising, relaxing, etc., and context that may affect the metrics, e.g., weather factors, location information, height information. Scheduling platform 111 may also determine existing medical conditions and prescriptions, and social detriments of health (SDOH). In one example, a regular patient's normal threshold range for fasting blood glucose is below 100, but for a diabetic patient, it is higher. Similarly, for medication intake, given user 101 consumes certain medication daily, a threshold may be set by user 102 that may be slightly deviated from existing industry thresholds. Scheduling platform 111 may compare the plurality of risk scores to a risk score threshold to determine the health conditions of user 101, wherein the health conditions indicate a low-risk condition, a moderate-risk condition, a high-risk condition, a severe-risk condition, or a critical-risk condition.

In step 313, scheduling platform 111 may determine a recent risk score for user 101 based on the plurality of risk score. More specifically, in one embodiment, scheduling platform 111 may determine a recent risk score for user 101 based on a change in the plurality of risk scores. In one embodiment, the recent risk score is indicative of a recent health condition trend of the user. In one embodiment, scheduling platform 111 may process the initial health dataset, the plurality of subsequent health datasets, or a combination thereof to determine historical risk scores of user 101 (e.g., at least a portion of the plurality of risk scores, determined based on a pre-determined time period). Scheduling platform 111 may analyze the historical risk scores of user 101 to determine the recent health condition trend for the user, wherein the recent health condition trend indicates an improving health condition, a deteriorating health condition, or a stable health condition.

In step 315, scheduling platform 111 may adjust the schedule of appointments for user 101 based on the recent risk score. The schedule of appointments may include one or more scheduled appointments. In one embodiment, scheduling platform 111 may process at least one database associated with user 102 to determine a plurality of other users with i) low-risk conditions and ii) appointments scheduled before user 101. Scheduling platform 111 may exchange at least one appointment in the schedule of appointments of user 101 with at least one of the appointments scheduled for the plurality of other users with low-risk conditions. In another embodiment, scheduling platform 111 may process at least one database associated with user 102 to determine a plurality of other users with i) high-risk conditions and ii) appointments scheduled after user 101. Scheduling platform 111 may exchange at least one appointment in the schedule of appointments of user 101 with at least one of the appointments scheduled for the plurality of other users with high-risk conditions. In another embodiment, scheduling platform 111 may determine the unavailability of user 102 during the adjusting of the schedule of appointments for user 101 based, at least in part, on the processing of the database associated with user 102. Scheduling platform 111 may transfer the appointment to at least one other user 102 based, at least in part, on location information, specialty information, availability information, or a combination thereof. In a further embodiment, scheduling platform 111 may monitor, in real-time or near real-time, contextual information that influences the schedule of appointments. The contextual information may include weather information, traffic information, availability information of user 101 and user 102, or a combination thereof. Scheduling platform 111 may dynamically update the schedule of appointments based, at least in part, on the monitoring.

In step 317, scheduling platform 111 may transmit a notification to UE 103 of user 101 indicating that the schedule of appointments has been adjusted. The notification may contain information that describes how the appointments are adjusted, e.g., whether they have been moved back, moved up, maintained the same, moved to a different healthcare provider, etc., and detailed information about each of the adjusted appointments. In one embodiment, the notification may include an aural notification, a visual notification, a tactile notification, or a combination thereof in a user interface of UE 103 associated with user 101.

Figure 4:
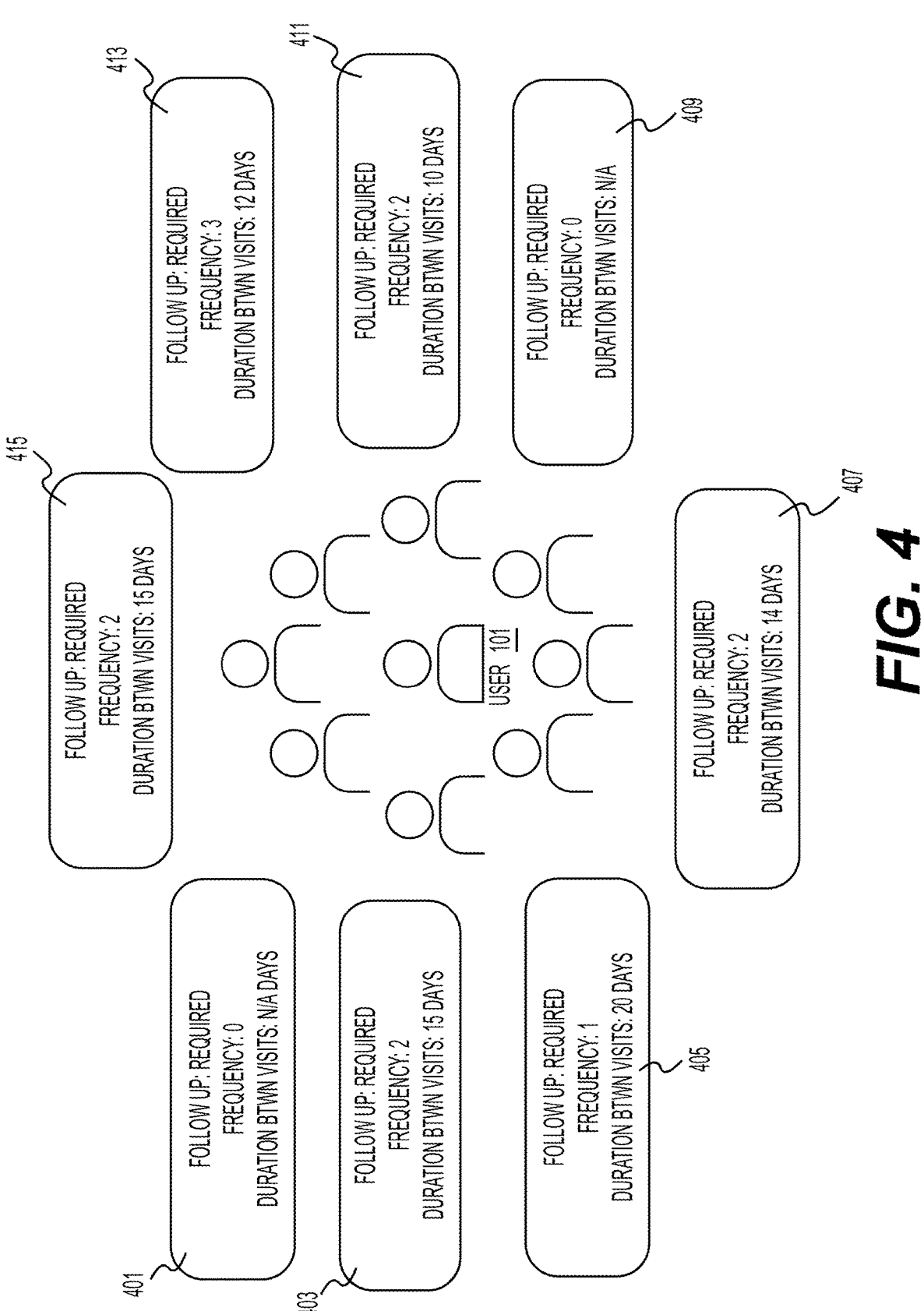
FIG. 4 is a diagram that represents a scenario wherein patients with similar health profiles are identified to determine a frequency of monitoring, a frequency of appointments, a duration between the appointments, and/or a type and length of the appointments for user 101, according to aspects of the disclosure.

FIG. 4 is a diagram that represents a scenario wherein other users (e.g., patients) with similar health profiles to user 101 (e.g., patient) are identified to determine a frequency of monitoring, a frequency of appointments, a duration between the appointments, and/or a type and length of the appointments for user 101, according to one example embodiment. In one example embodiment, scheduling platform 111 may receive and monitor the health profile of user 101 at the time of the appointment, e.g., t=0, and may determine a need for continuous care monitoring, e.g., remote patient monitoring. Alternatively or additionally, scheduling platform 111 may receive the health profile of user 101 ahead of the appointment. Scheduling platform 111 may set a frequency of monitoring and a channel for care at the time of appointment. Scheduling platform 111 may analyze anonymized health dataset available with user 102, by using trained machine learning module 211 that implements various analytics techniques, e.g., K-nearest neighbors' algorithm, to identify patients with similar health profiles and then process the profiles to determine the need for continuous care monitoring. Scheduling platform 111 may then estimate the frequency of appointments, tentative duration between the appointments, and/or type and length of the appointments, e.g., telemedicine or in-person. Such an evidence-based clinical decision support system is eventually authorized by user 102. Furthermore, scheduling platform 111 may add more weights to the appointment parameters of user 101 for achieving better outcomes, and such addition of weights may be tracked over time to add more value to the scheduling process.

In one example embodiment, user 101 is diagnosed with a kidney stone. Scheduling platform 111 may study the health profile of user 101 at time t=0, and may determine the following feature for user 101:

Diagnosis: Kidney Stone

Size: 10.5 mm

Gender: F

Age: 45 Yrs

Labs1: values from kidney function test (KFTs), other tests.

other parameters . . . .

Scheduling platform 111, via machine learning module 211, may locate k-nearest neighbors to the profile of user 101, i.e., patients with similar health profiles as user 101, and may analyze past appointment schedules and other parameters of these patients to estimate the frequency of monitoring, frequency of appointments, duration between appointments, type and length of the appointments, etc. In one embodiment, one of the critical parameters used in the evaluation may be the health outcome, e.g., positive vs negative, of the other patients with similar conditions and co-morbidities.

In this example embodiment, scheduling platform 111 may identify eight patients, e.g., patients 401 through 415, with similar health profiles to that of user 101. Scheduling platform 111 may process and evaluate the health profiles of patients 401 through 415 to understand the reaction of patients 401 through 415 to the disease and the distribution of appointment schedules. Scheduling platform 111 may then determine the probability of follow-up for user A is 0.75, the frequency of appointments for user A is 2, and the tentative duration between the appointments is 14.33 (14 days). The channel of care or any other relevant information may be evaluated in such a fashion. It should be understood that K-nearest neighbors is one of the techniques implemented by scheduling platform 111, and any other machine learning algorithms may be implemented by scheduling platform 111.

Figure 5:
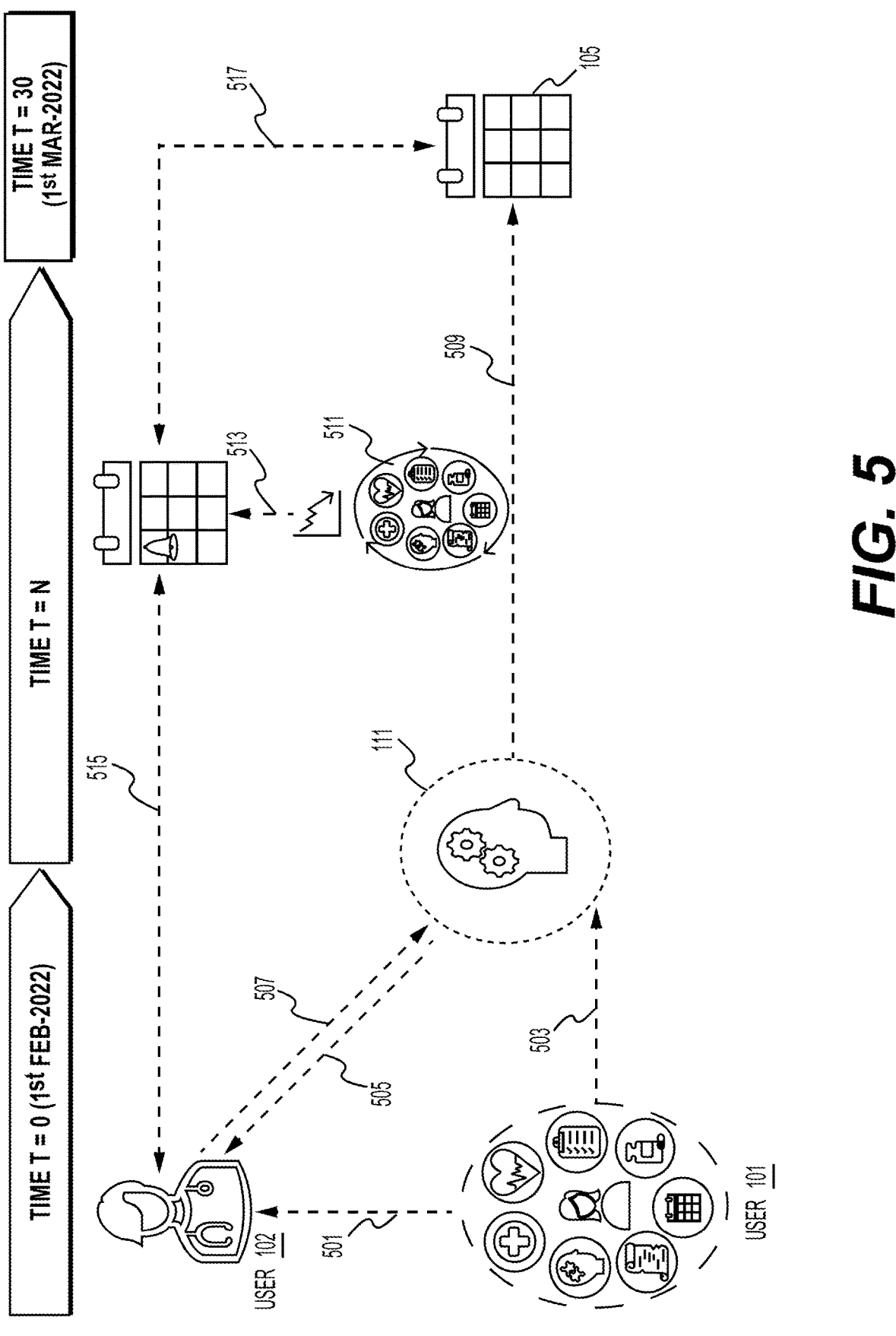
FIG. 5 is a diagram that illustrates an evidence-based clinical decision system that tracks a patient's needs during treatment and optimally schedules or dynamically reschedules upcoming appointments based on a real-time analysis of the patient's changing health conditions, according to aspects of the disclosure.

FIG. 5 is a diagram that illustrates an evidence-based clinical decision system that tracks a patient's needs during treatment and optimally schedules or dynamically reschedules upcoming appointments based on real-time analysis of the patient's changing health conditions, according to one example embodiment. In one example embodiment, user 101 visits user 102, for a health check-up, whereupon user 102 undertakes a diagnosis of user 101 (step 501). In step 503, scheduling platform 111 may receive, via one or more sensors 107, health-related data of user 101, the health-related data is processed to estimate or predict upcoming appointment dates for user 101. Scheduling platform 111 may communicate the estimated or predicted upcoming appointment dates to user 102 for approval (step 505). In step 507, user 102 may review and approve the proposed appointment dates, whereupon scheduling platform 111 receives authorization to register the date. In step 509, scheduling platform 111 may block, or add, the appointment dates for user 101 in calendar application 105 of user 102.

Upon reserving the scheduled appointment for user 101, scheduling platform 111 may monitor, in real-time or near real-time, the changing health conditions of user 101 (step 511). Scheduling platform 111 may generate risk scores for user 101 based, at least in part on, the health scores, rule scores, or medication scores. In step 513, scheduling platform 111 may dynamically adjust the schedule of appointments for user 101 based on the recent risk score. Scheduling platform 111 may alert user 102 on the health condition of user 101 and the recommended rescheduling of the appointment at a specific date to prevent health risk (step 515). Upon approval from user 102, scheduling platform 111 may overwrite the previously scheduled appointment from user 101 with the newly rescheduled appointment date, and the same is reflected in calendar application 105 of user 102 (step 517).

In one example embodiment, user A, a 70-year-old man with multiple chronic medical problems including chronic obstructive pulmonary disease (COPD) recently became infected with an infectious disease, the symptoms include coughing but no shortness of breath. User A has received vaccination as well as an antibody infusion and is scheduled for a follow-up with a healthcare professional on a monthly basis. Scheduling platform 111 may recommend rescheduling the appointments to a telemedicine visit in 1 week and a subsequent in-person visit 2 weeks thereafter based on characteristics and health score findings for user 101. Scheduling platform 111 may continue with the ongoing remote monitoring of user 101, and may determine a further decline in the health conditions of user 101, i.e., an increased health risk score, due to falling oxygen level. Scheduling platform 111 may generate a recommendation to reschedule the in-person visit immediately, and an alert is triggered by locating the best available appointment slot for user 101.

In another example embodiment, user B, a 65-year-old patient with Asthma, is provided with a remote patient monitoring facility per the recommendation of user 102. Scheduling platform 111 may detect a flair in the symptoms over the past week and an evident decline in health parameters, i.e., a drastic increase in health risk score. Scheduling platform 111 may recommend an immediate telemedicine consultation by notifying user 102, and that user B is started on an oral steroid immediately. Scheduling platform 111 upon approval from user 102 may recommend a follow-up in two days as per standard care, however, no appointments are available with user 102. Scheduling platform 111 may swap appointment dates with another patient with a low-risk score. Scheduling platform 111 may also recommend continuing remote patient monitoring during this acute phase of illness.

Figure 6A:
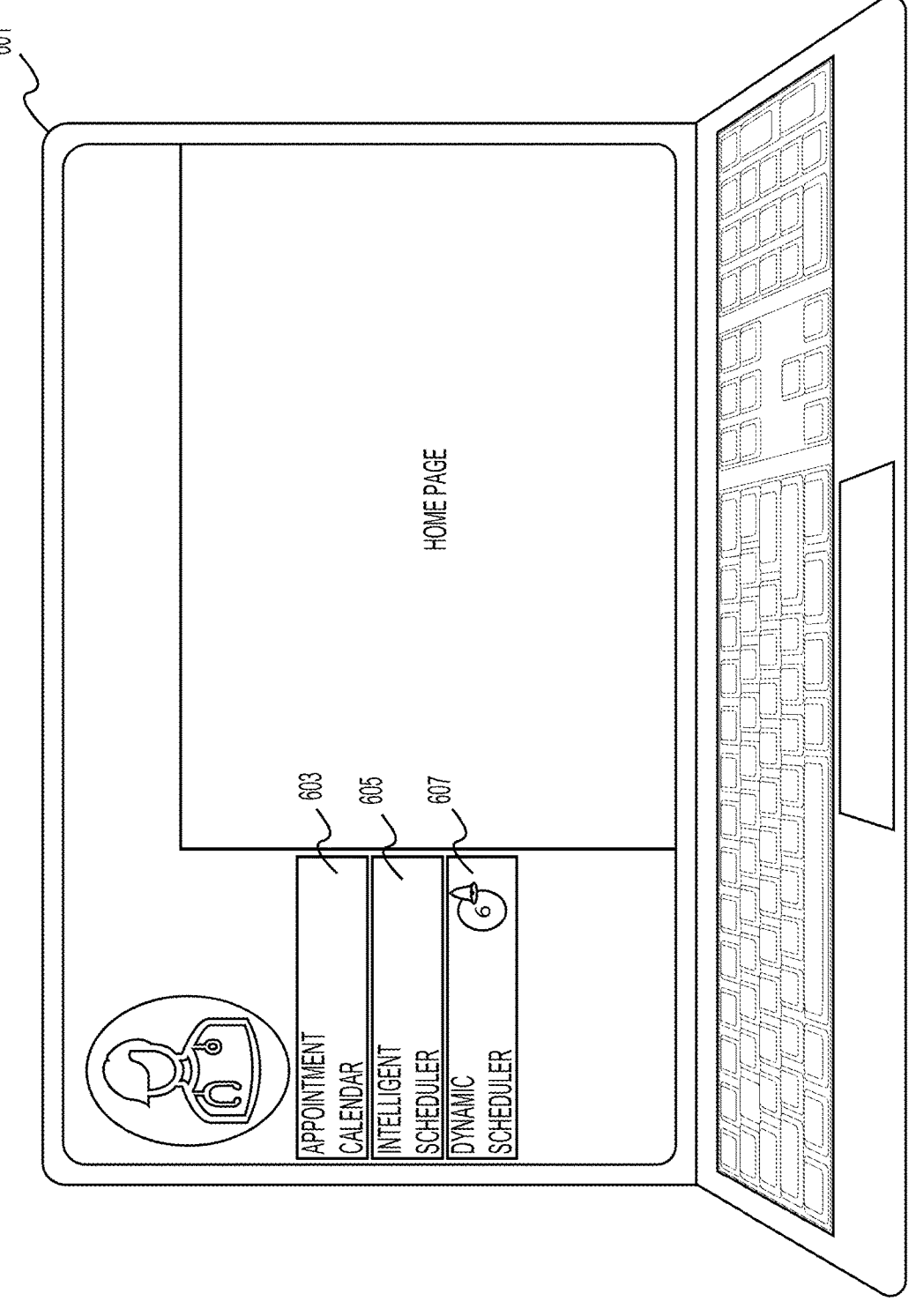
FIGS. 6A through 6C are user interface diagrams that illustrate dynamic scheduling of health appointments for patients based on their changing health conditions, according to one example embodiment.
Figure 6B:
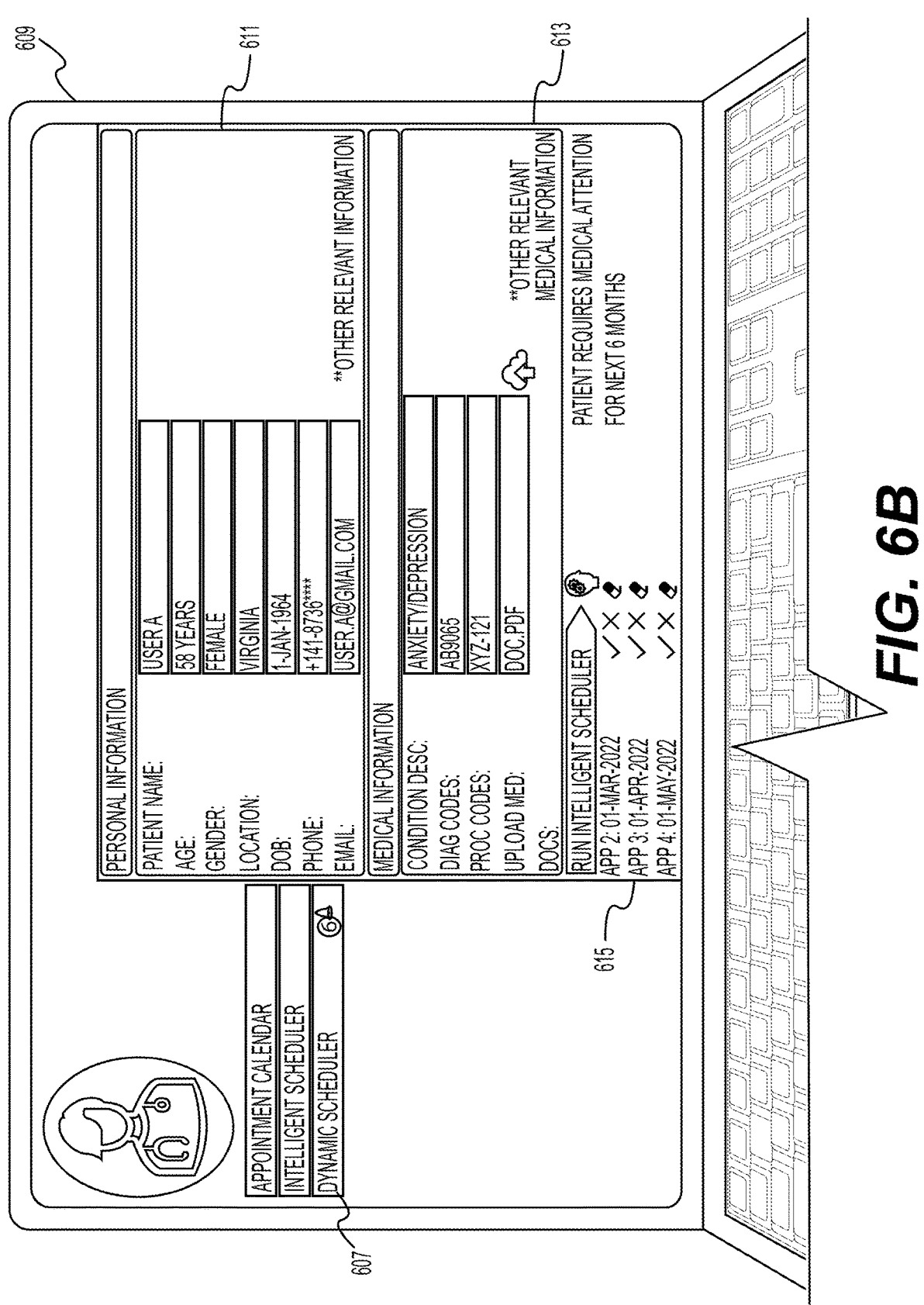
Figure 6C:
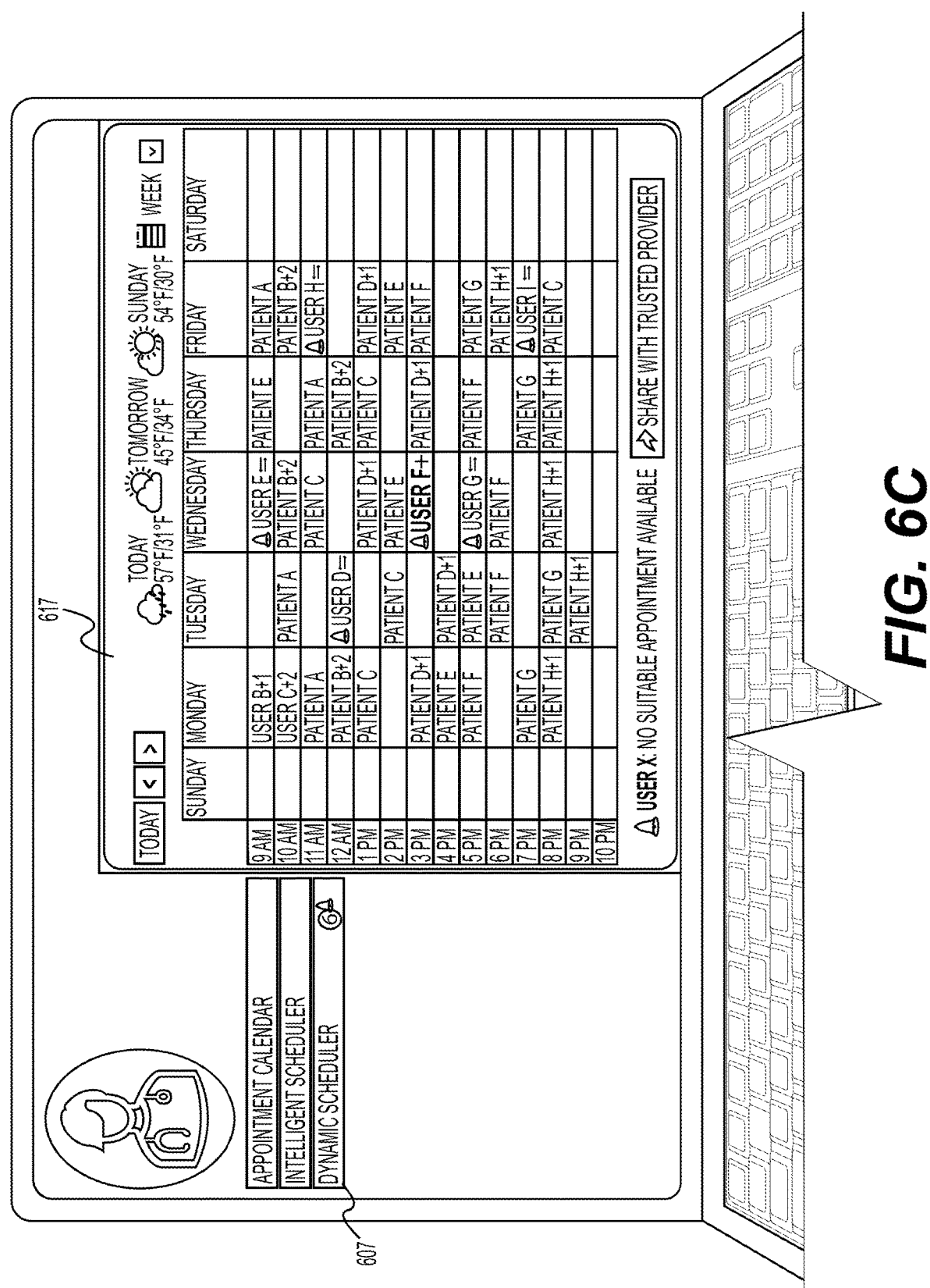

FIGS. 6A through 6C are user interface diagrams that illustrate dynamic scheduling of health appointments for user 101 based on changing health conditions, according to one example embodiment. FIG. 6A depicts a main entry screen 601 for an online health-related service, e.g., an online appointment scheduling service. The main entry screen 601 includes a plurality of icons, e.g., appointment calendar 603, intelligent scheduler 605, and dynamic scheduler 607 that may invoke different functions related to appointment scheduling. In one embodiment, intelligent scheduler 605 may be utilized to set up the first set of appointments and monitoring recommendations based, at least in part, on initial data collection and evaluation of the health condition of user 101, appointment information collected from a plurality of similar-looking profiles via machine learning (ML) models, or a combination thereof. In one embodiment, dynamic scheduler 607 may be utilized to monitor and reschedule in real-time or near real-time scheduled appointments based, at least in part, on changing health conditions, e.g., improvement or deterioration in health parameters, of user 101. In this example embodiment, user 102 may select intelligent scheduler 605, whereupon user 102 is navigated to screen 609 of FIG. 6B. During or after the health appointment, user 102 may enter personal information 611 and medical information 613 of user 101. In one embodiment, personal information 611 and medical information 613 may be automatically populated by scheduling platform 111. Scheduling platform 111 may then process personal information 611 and medical information 613 to generate a recommendation of tentative appointment dates 615, and may communicate the recommendation to user 102. In one embodiment, user 102 may approve the recommended dates, and scheduling platform 111 may add the dates to an appointment calendar of user 102. In another embodiment, user 102 may overwrite the recommended dates and may enter a new date based on the initial assessment of the health condition of user 101.

In this example embodiment, scheduling platform 111 may determine deterioration in the health condition of user 101 and may notify user 102 to dynamically reschedule the scheduled appointment, and seek their approval to book the new appointment by overriding the previously scheduled appointment. Once approved by user 102, scheduling platform 111 may add the new appointment date to calendar 617 by canceling the previously scheduled appointment. Scheduling platform 111 may send notifications to user 101 regarding the new appointment. Scheduling platform 111 may also track external factors, e.g., weather forecasts, user 101's calendar/availability, user 102's calendar/availability, etc., that may lead to cancellation of the appointment while setting up the dynamic changes.

Figure 7A:
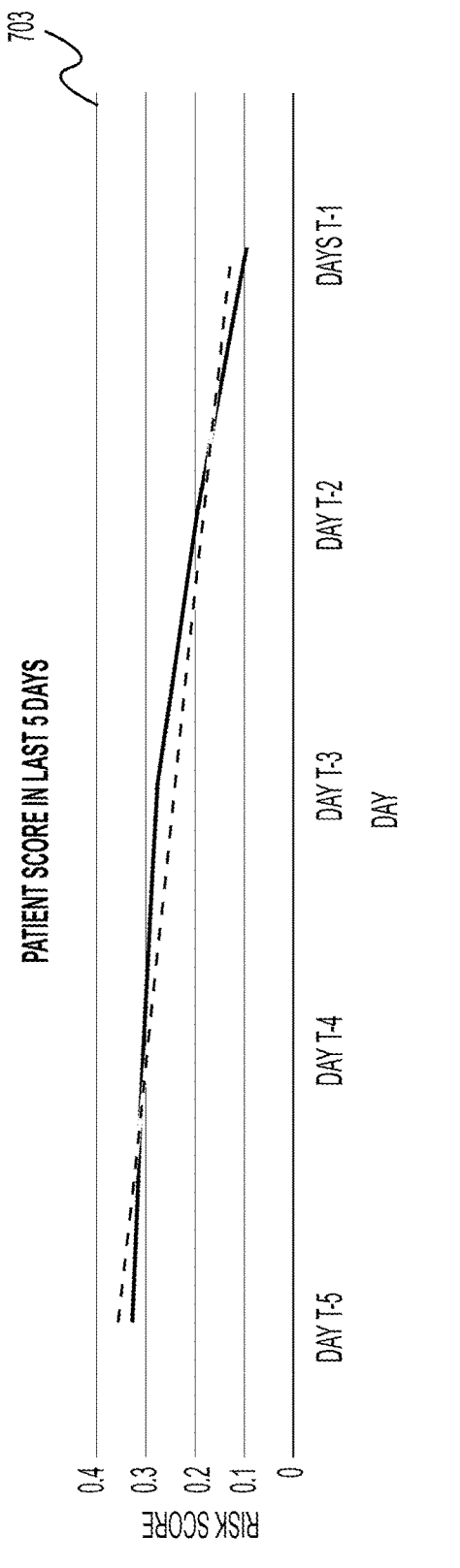
FIGS. 7A and 7B are diagrams for calculating recent risk scores, according to aspects of the disclosure.
Figure 7B:
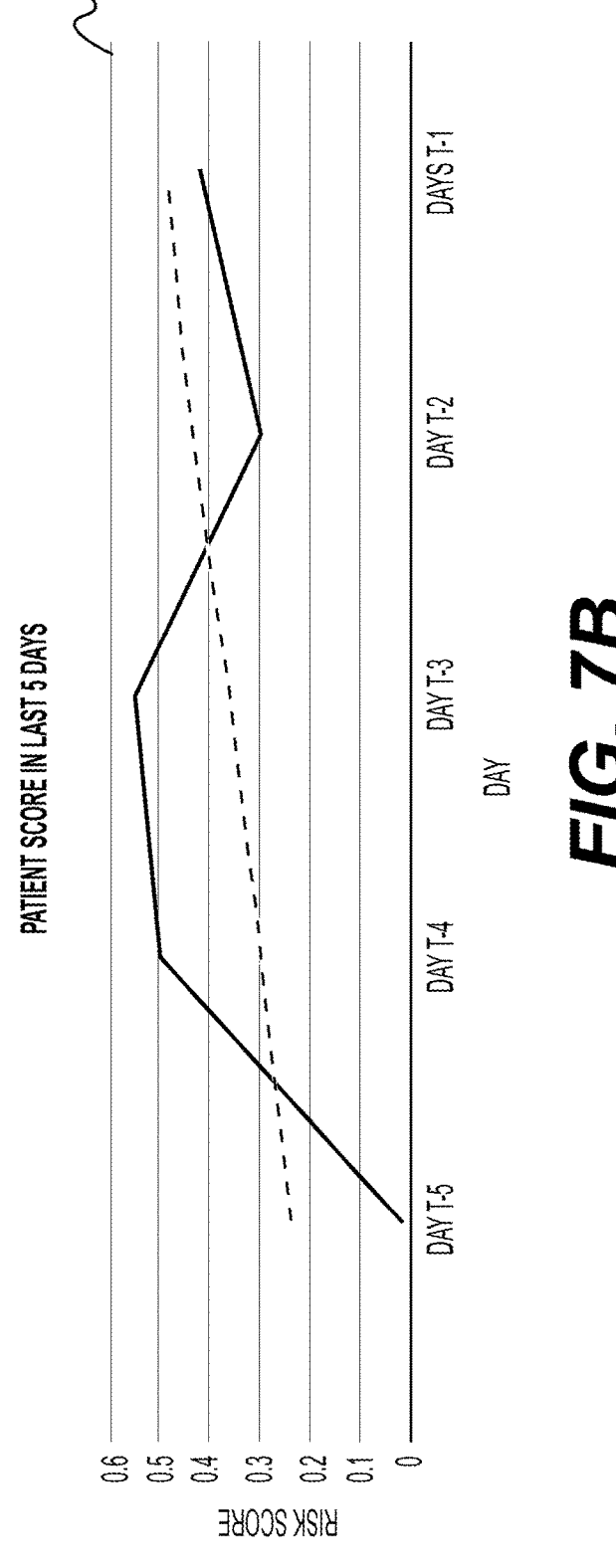

FIGS. 7A and 7B are diagrams for calculating recent risk scores, according to one example embodiment. As depicted in table 701 and graph 703 of FIG. 7A, scheduling platform 111 may collect risk scores of user A for a pre-determined time period, e.g., 5 days, to analyze changes in the risk scores. Any changes in the risk scores may indicate an improvement, a deterioration, or a constant health condition of user A. In this example, the scores of user A are:

Score at time T (Present Day Score)=0.02 (low risk)
Recent Score avg=0.20 (low risk) (may also be weighed towards recent data/weighted average)
Rate of change=−0.062 (improving health/reducing Risk)
The recent risk score is:
Recent Risk Score=0.11 [Direction=−ve, improving health conditions]

The calculated recent risk score is within the low-risk range and the condition of user A is improving, e.g., a daily decline in the risk score indicated by the negative sign in the rate of change, hence there is no requirement for rescheduling the appointment for user A, e.g., preponing the appointment. Although the appointment may be delayed, canceled, or swapped with an appointment scheduled for another user with a recent risk score indicative of declining health condition, depending on the threshold set on appointment scheduler of user 102.

On the other hand, as illustrated in table 705 and graph 707 of FIG. 7B, scheduling platform 111 may collect risk scores of user B for a pre-determined time period, e.g., 5 days, to analyze changes in the risk scores. Any changes in the risk scores may indicate an improvement, a deterioration, or a constant health condition of user B. In this example, the scores of user B are:

Score at time T=0.44 (high risk)
Recent Score avg=0.37 (moderate risk) (may also be weighted
towards more recent data/weighted average)
Rate of change=+0.084 (declining health/Increasing Risk)
The recent risk score is:

Recent Risk Score=0.41[Direction=+ve,declining health conditions]

The calculated recent risk score is within the moderate to the high-risk range and the health condition of user B is deteriorating, e.g., a daily increase in risk scores indicated by the positive sign in the rate of change. Hence, there is a requirement to reschedule the health appointment for user B as soon as possible. It is understood that calculating the recent score average and the rate of change is one of numerous methods to determine recent risk scores. The recent risk scores may be calculated by any other methods per requirement, e.g., slope calculation, trend evaluations, etc.

FIG. 7C is a diagram that represents the dynamic exchanging of health appointments between patients based on their health scores, according to one example embodiment. As depicted, scheduling platform 111 may process an appointment database, e.g., calendar application, associated with user 102 to determine appointment schedules for a plurality of patients. Scheduling platform 111 may classify appointment database based on the risk scores and the date of appointment of the patients, e.g., user A with high-risk scores (i.e., a recent risk core indicative of at least one of i) high risk or ii) declining health condition) and appointment far off from the present date is placed in table 709 whilst user H with low-risk scores (i.e., a recent risk score indicative of at least one of i) low risk or ii) improving health condition) and appointment nearby is positioned in table 711. Scheduling platform 111 may swap the appointment dates between the patients in tables 709 and 711, and the calendar application may be updated with new appointment schedules. In this example embodiment, scheduling platform 111 may determine that user A is at a critical health risk and requires immediate attention, but his next appointment is 15 days from the present date. Scheduling platform 111 may seek permission to access the appointment schedules of user 102, and upon receiving access may automatically find the next closest empty spot available and may dynamically move the appointment of user A to that date. On the other hand, if empty spots are not available, scheduling platform 111 may automatically evaluate the appointments which may be delayed or canceled, e.g., patients with extremely low risk, and may decide to cancel or delay their appointments, e.g., appointment date of user A may be swapped with appointment date of user H. Scheduling platform 111 may also seek permission to automatically move or transfer the appointment of user A to a trusted provider in case of unavailability of user 102 and user A needs critical care.

Figure 8:
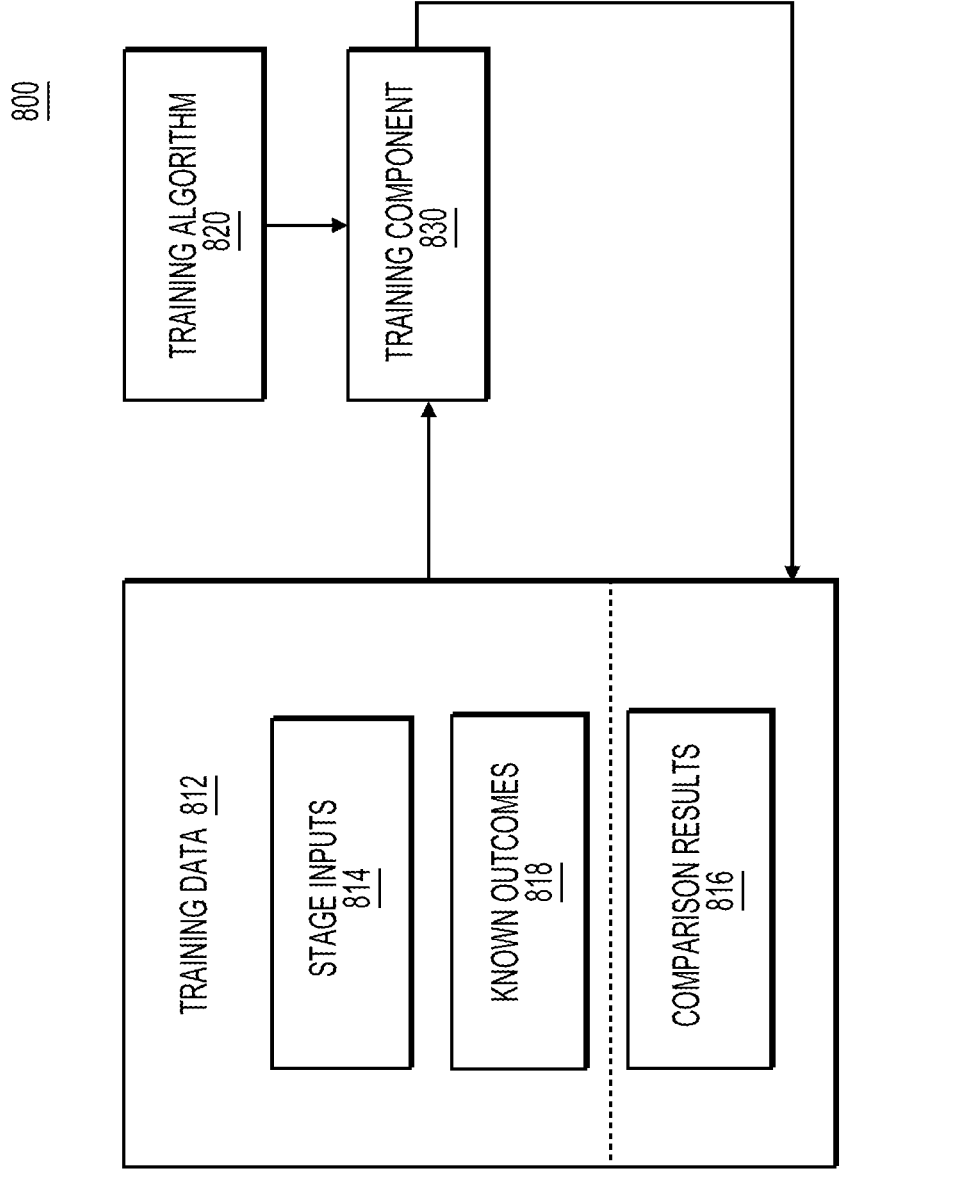
FIG. 8 shows an example machine learning training flow chart.

One or more implementations disclosed herein include and/or may be implemented using machine learning model, e.g., machine learning module 211. For example, one or more of the modules of scheduling platform 111 may be implemented using a machine learning model and/or may be used to train the machine learning model, e.g., training module 209. A given machine learning model may be trained using the data flow 800 of FIG. 8. Training data 812 may include one or more of stage inputs 814 and known outcomes 818 related to the machine learning model to be trained. The stage inputs 814 may be from any applicable source including text, visual representations, data, values, comparisons, stage outputs, e.g., one or more outputs from one or more steps from FIG. 3. The known outcomes 818 may be included for the machine learning models generated based on supervised or semi-supervised training. An unsupervised machine learning model may not be trained using known outcomes 818. Known outcomes 818 may include known or desired outputs for future inputs similar to or in the same category as stage inputs 814 that do not have corresponding known outputs.

The training data 812 and a training algorithm 820, e.g., one or more of the modules implemented using the machine learning model and/or may be used to train the machine learning model, may be provided to a training component 830 that may apply the training data 812 to the training algorithm 820 to generate the machine learning model. According to an implementation, the training component 830 may be provided comparison results 816 that compare a previous output of the corresponding machine learning model to apply the previous result to re-train the machine learning model. The comparison results 816 may be used by training component 830 to update the corresponding machine learning model. The training algorithm 820 may utilize machine learning networks and/or models including, but not limited to a deep learning network such as Deep Neural Networks (DNN), Convolutional Neural Networks (CNN), Fully Convolutional Networks (FCN) and Recurrent Neural Networks (RCN), probabilistic models such as Bayesian Networks and Graphical Models, classifiers such as K-Nearest Neighbors, and/or discriminative models such as Decision Forests and maximum margin methods, or the like.

The machine learning model used herein may be trained and/or used by adjusting one or more weights and/or one or more layers of the machine learning model. For example, during training, a given weight may be adjusted (e.g., increased, decreased, removed) based on training data or input data. Similarly, a layer may be updated, added, or removed based on training data/and or input data. The resulting outputs may be adjusted based on the adjusted weights and/or layers.

In general, any process or operation discussed in this disclosure that is understood to be computer-implementable, such as the process illustrated in FIG. 3 may be performed by one or more processors of a computer system as described herein. A process or process step performed by one or more processors may also be referred to as an operation. The one or more processors may be configured to perform such processes by having access to instructions (e.g., software or computer-readable code) that, when executed by the one or more processors, cause the one or more processors to perform the processes. The instructions may be stored in a memory of the computer system. A processor may be a central processing unit (CPU), a graphics processing unit (GPU), or any suitable types of processing unit.

A computer system, such as a system or device implementing a process or operation in the examples above, may include one or more computing devices. One or more processors of a computer system may be included in a single computing device or distributed among a plurality of computing devices. One or more processors of a computer system may be connected to a data storage device. A memory of the computer system may include the respective memory of each computing device of the plurality of computing devices.

FIG. 9 illustrates an implementation of a general computer system that may execute techniques presented herein. The computer system 900 can include a set of instructions that can be executed to cause the computer system 900 to perform any one or more of the methods or computer based functions disclosed herein. The computer system 900 may operate as a standalone device or may be connected, e.g., using a network, to other computer systems or peripheral devices.

Unless specifically stated otherwise, as apparent from the following discussions, it is appreciated that throughout the specification, discussions utilizing terms such as "processing," "computing," "calculating," "determining", "analyzing" or the like, refer to the action and/or processes of a computer or computing system, or similar electronic computing device, that manipulate and/or transform data represented as physical, such as electronic, quantities into other data similarly represented as physical quantities.

In a similar manner, the term "processor" may refer to any device or portion of a device that processes electronic data, e.g., from registers and/or memory to transform that electronic data into other electronic data that, e.g., may be stored in registers and/or memory. A "computer," a "computing machine," a "computing platform," a "computing device," or a "server" may include one or more processors.

In a networked deployment, the computer system 900 may operate in the capacity of a server or as a client user computer in a server-client user network environment, or as a peer computer system in a peer-to-peer (or distributed) network environment. The computer system 900 can also be implemented as or incorporated into various devices, such as a personal computer (PC), a tablet PC, a set-top box (STB), a personal digital assistant (PDA), a mobile device, a palmtop computer, a laptop computer, a desktop computer, a communications device, a wireless telephone, a land-line telephone, a control system, a camera, a scanner, a facsimile machine, a printer, a pager, a personal trusted device, a web appliance, a network router, switch or bridge, or any other machine capable of executing a set of instructions (sequential or otherwise) that specify actions to be taken by that machine. In a particular implementation, the computer system 900 can be implemented using electronic devices that provide voice, video, or data communication. Further, while a computer system 900 is illustrated as a single system, the term "system" shall also be taken to include any collection of systems or sub-systems that individually or jointly execute a set, or multiple sets, of instructions to perform one or more computer functions.

As illustrated in FIG. 9, the computer system 900 may include a processor 902, e.g., a central processing unit (CPU), a graphics processing unit (GPU), or both. The processor 902 may be a component in a variety of systems. For example, the processor 902 may be part of a standard personal computer or a workstation. The processor 902 may be one or more general processors, digital signal processors, application specific integrated circuits, field programmable gate arrays, servers, networks, digital circuits, analog circuits, combinations thereof, or other now known or later developed devices for analyzing and processing data. The processor 902 may implement a software program, such as code generated manually (i.e., programmed).

The computer system 900 may include a memory 904 that can communicate via a bus 908. The memory 904 may be a main memory, a static memory, or a dynamic memory. The memory 904 may include, but is not limited to computer readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one implementation, the memory 904 includes a cache or random-access memory for the processor 902. In alternative implementations, the memory 904 is separate from the processor 902, such as a cache memory of a processor, the system memory, or other memory. The memory 904 may be an external storage device or database for storing data. Examples include a hard drive, compact disc ("CD"), digital video disc ("DVD"), memory card, memory stick, floppy disc, universal serial bus ("USB") memory device, or any other device operative to store data. The memory 904 is operable to store instructions executable by the processor 902. The functions, acts or tasks illustrated in the figures or described herein may be performed by the processor 902 executing the instructions stored in the memory 904. The functions, acts or tasks are independent of the particular type of instructions set, storage media, processor or processing strategy and may be performed by software, hardware, integrated circuits, firm-ware, micro-code and the like, operating alone or in combination. Likewise, processing strategies may include multiprocessing, multitasking, parallel processing and the like.

As shown, the computer system 900 may further include a display 910, such as a liquid crystal display (LCD), an organic light emitting diode (OLED), a flat panel display, a solid-state display, a cathode ray tube (CRT), a projector, a printer or other now known or later developed display device for outputting determined information. The display 910 may act as an interface for the user to see the functioning of the processor 902, or specifically as an interface with the software stored in the memory 904 or in the drive unit 906.

Additionally or alternatively, the computer system 900 may include an input/output device 912 configured to allow a user to interact with any of the components of computer system 900. The input/output device 912 may be a number pad, a keyboard, or a cursor control device, such as a mouse, or a joystick, touch screen display, remote control, or any other device operative to interact with the computer system 900.

The computer system 900 may also or alternatively include drive unit 906 implemented as a disk or optical drive. The drive unit 906 may include a computer-readable medium 922 in which one or more sets of instructions 924, e.g. software, can be embedded. Further, instructions 924 may embody one or more of the methods or logic as described herein. The instructions 924 may reside completely or partially within the memory 904 and/or within the processor 902 during execution by the computer system 900. The memory 904 and the processor 902 also may include computer-readable media as discussed above.

In some systems, a computer-readable medium 922 includes instructions 924 or receives and executes instructions 924 responsive to a propagated signal so that a device connected to a network 930 can communicate voice, video, audio, images, or any other data over the network 930. Further, the instructions 924 may be transmitted or received over the network 930 via a communication port or interface 920, and/or using a bus 908. The communication port or interface 920 may be a part of the processor 902 or may be a separate component. The communication port or interface 920 may be created in software or may be a physical connection in hardware. The communication port or interface 920 may be configured to connect with a network 930, external media, the display 910, or any other components in computer system 900, or combinations thereof. The connection with the network 930 may be a physical connection, such as a wired Ethernet connection or may be established wirelessly as discussed below. Likewise, the additional connections with other components of the computer system 900 may be physical connections or may be established wirelessly. The network 930 may alternatively be directly connected to a bus 908.

While the computer-readable medium 922 is shown to be a single medium, the term "computer-readable medium" may include a single medium or multiple media, such as a centralized or distributed database, and/or associated caches and servers that store one or more sets of instructions. The term "computer-readable medium" may also include any medium that is capable of storing, encoding, or carrying a set of instructions for execution by a processor or that cause a computer system to perform any one or more of the methods or operations disclosed herein. The computer-readable medium 922 may be non-transitory, and may be tangible.

The computer-readable medium 922 can include a solid-state memory such as a memory card or other package that houses one or more non-volatile read-only memories. The computer-readable medium 922 can be a random-access memory or other volatile re-writable memory. Additionally or alternatively, the computer-readable medium 922 can include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is a tangible storage medium. Accordingly, the disclosure is considered to include any one or more of a computer-readable medium or a distribution medium and other equivalents and successor media, in which data or instructions may be stored.

In an alternative implementation, dedicated hardware implementations, such as application specific integrated circuits, programmable logic arrays and other hardware devices, can be constructed to implement one or more of the methods described herein. Applications that may include the apparatus and systems of various implementations can broadly include a variety of electronic and computer systems. One or more implementations described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

The computer system 900 may be connected to a network 930. The network 930 may define one or more networks including wired or wireless networks. The wireless network may be a cellular telephone network, an 802.11, 802.16, 802.20, or WiMAX network. Further, such networks may include a public network, such as the Internet, a private network, such as an intranet, or combinations thereof, and may utilize a variety of networking protocols now available or later developed including, but not limited to TCP/IP based networking protocols. The network 930 may include wide area networks (WAN), such as the Internet, local area networks (LAN), campus area networks, metropolitan area networks, a direct connection such as through a Universal Serial Bus (USB) port, or any other networks that may allow for data communication. The network 930 may be configured to couple one computing device to another computing device to enable communication of data between the devices. The network 930 may generally be enabled to employ any form of machine-readable media for communicating information from one device to another. The network 930 may include communication methods by which information may travel between computing devices. The network 930 may be divided into sub-networks. The sub-networks may allow access to all of the other components connected thereto or the sub-networks may restrict access between the components. The network 930 may be regarded as a public or private network connection and may include, for example, a virtual private network or an encryption or other security mechanism employed over the public Internet, or the like.

In accordance with various implementations of the present disclosure, the methods described herein may be implemented by software programs executable by a computer system. Further, in an exemplary, non-limited implementation, implementations can include distributed processing, component/object distributed processing, and parallel processing. Alternatively, virtual computer system processing can be constructed to implement one or more of the methods or functionality as described herein.

Although the present specification describes components and functions that may be implemented in particular implementations with reference to particular standards and protocols, the disclosure is not limited to such standards and protocols. For example, standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same or similar functions as those disclosed herein are considered equivalents thereof.

It will be understood that the steps of methods discussed are performed in one embodiment by an appropriate processor (or processors) of a processing (i.e., computer) system executing instructions (computer-readable code) stored in storage. It will also be understood that the disclosure is not limited to any particular implementation or programming technique and that the disclosure may be implemented using any appropriate techniques for implementing the functionality described herein. The disclosure is not limited to any particular programming language or operating system.

It should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations and implementations are possible within the scope of the disclosure. Accordingly, the disclosure is not to be restricted except in light of the attached claims and their equivalents.

What is claimed is:

1. A computer-implemented method for scheduling appointments based on changing health conditions of users, comprising:

receiving, by one or more processors and via one or more sensors at a first time, an initial health dataset of a user, wherein the initial health dataset indicates a health condition of the user;

applying, by the one or more processors, a trained machine learning model to the initial health dataset to determine i) a second time to schedule an appointment for the user with a service provider, and ii) a frequency for monitoring a plurality of subsequent health datasets between the first time and the second time, wherein the trained machine learning model is configured to identify one or more other users with similar health profiles to the user and determine the second time and the frequency for monitoring based on the similar health profiles;

scheduling, by the one or more processors, the appointment for the user at the second time;

receiving, by the one or more processors and via the one or more sensors after the first time and before the second time, the plurality of subsequent health datasets of the user, wherein the plurality of subsequent health datasets is received at an interval based on the frequency of monitoring;

determining, by the one or more processors and based on a processing of the plurality of subsequent health datasets, at least one of health scores, rule scores, or medication scores for the user;

determining, by the one or more processors, a plurality of risk scores corresponding to the plurality of subsequent health datasets for the user based on the at least one of the health scores, the rule scores, or the medication scores, wherein the plurality of risk scores are compared to a risk score threshold to determine a risk associated with one or more health conditions of the user, including at least the health condition indicated by the initial health dataset, and wherein the risk associated with the one or more health conditions indicates a low-risk condition, a moderate-risk condition, a high-risk condition, a severe-risk condition, or a critical-risk condition;

determining, by the one or more processors, a recent risk score, from among the plurality of risk scores for the user, has changed by a threshold level within a predefined time period, wherein the change in the recent risk score is indicative of a recent health condition trend of the user associated with a deterioration of the health condition indicated by the initial health dataset;

adjusting, by the one or more processors, the scheduling of the appointment for the user from the second time to a third time, the third time being prior to the second time based on the risk associated with the recent risk score;

determining, by the one or more processors and based on the initial health dataset and the plurality of subsequent health datasets, a treatment to respond to the deterioration of the health condition; and transmitting, by the one or more processors, a notification to a device associated with the user, the transmitting causing the device to display the notification about the adjusted scheduling of the appointment, wherein the determined treatment to respond to the deterioration of the health condition is administered to the user at the third time of the adjusted appointment.

2. The computer-implemented method of claim 1, wherein determining the recent risk score further comprises:

analyzing, by the one or more processors, at least a portion of the plurality of risk scores for the user to determine the recent health condition trend of the user, wherein at least the portion of the plurality of risk scores for the user is determined based on the predefined time period.

3. The computer-implemented method of claim 1, wherein adjusting the scheduling of the appointment further comprises:

processing, by the one or more processors, at least one database associated with the service provider to determine a plurality of other users with i) low-risk conditions and ii) appointments scheduled before the second time; and exchanging the appointment for the user at the second time with the adjusted appointment scheduled for one of the plurality of other users with low-risk conditions at the third time.

4. The computer-implemented method of claim 1, further comprising:

processing, by the one or more processors, at least one database associated with the service provider to determine a plurality of other users with i) low-risk conditions and ii) appointments scheduled before the second time;

determining, by the one or more processors, unavailability of the service provider based, at least in part, on the processing of the at least one database associated with the service provider; and transferring, by the one or more processors, the adjusted appointment at the third time to at least one other service provider based, at least in part, on location information, specialty information, availability information, or a combination thereof.

5. The computer-implemented method of claim 1, further comprising:

monitoring, by the one or more processors and in real-time or near real-time, contextual information that influences appointment scheduling, wherein the contextual information includes weather information, traffic information, availability information of the user and the service provider, or a combination thereof; and dynamically updating, by the one or more processors, the scheduling of the appointment based, at least in part, on the monitoring.

6. The computer-implemented method of claim 1, wherein the initial health dataset and the plurality of subsequent health datasets include health-related data, medical records, clinical data, appointment schedules, location information, preference information, insurance information, access credentials, or a combination thereof.

7. The computer-implemented method of claim 1, wherein the trained machine learning model applies a supervised machine learning algorithm, and wherein the supervised machine learning algorithm includes K-nearest neighbors.

8. The computer-implemented method of claim 1, wherein the displayed notification includes a user interface configured to enable the user to provide input associated with the adjusted scheduling of the appointment, and the method further comprising:

receiving, from the device associated with the user via the user interface, input from the user, the input including at least a consent associated with the adjusted scheduling of the appointment; and providing the input from the user as true labels to the trained machine learning model for retraining the trained machine learning model.

9. The computer-implemented method of claim 1, wherein at least the health scores are determined for the user, and determining the health scores comprises:

processing the plurality of subsequent health datasets to determine a plurality of health parameters of the user; and determining the health scores based on one or more of the plurality of health parameters.

10. The computer-implemented method of claim 9, wherein the plurality of health parameters include blood pressure, body temperature, skin temperature, heart rate variability, breathing rate, blood glucose levels, oxygen saturation levels, stress levels, or a combination thereof of the user.

11. The computer-implemented method of claim 1, wherein at least the rule scores are determined for the user, and determining the rule scores comprises:

receiving, via one or more devices associated with the service provider, a customized rule set for the user;

processing the plurality of subsequent health datasets to determine an adherence to the customized rule set or a deviation from the customized rule set; and determining the rule scores based on the adherence to the customized rule set or the deviation from the customized rule set by applying weighted sets to the customized rule set.

12. The computer-implemented method of claim 11, wherein the customized rule set for the user includes physical activities for a predetermined time period, a body mass index (BMI) range, a prescribed diet, laboratory test values, or a combination thereof for the user.

13. The computer-implemented method of claim 1, wherein at least the medication scores are determined for the user, and determining the medication scores comprises:

receiving, via the one or more sensors, a plurality of images, a plurality of video sequences, or a combination thereof representative of an adherence or a deviation by the user to a prescribed medication; and processing the plurality of images, the plurality of video sequences, or a combination thereof to generate the medication scores for the user.

14. The computer-implemented method of claim 1, wherein the trained machine learning model is further configured to determine a channel for the appointment, wherein the channel includes an in-person healthcare service or a remote healthcare service.

15. The computer-implemented method of claim 14, wherein the channel for the appointment determined by the trained machine learning model is a first channel, and adjusting the scheduling of the appointment further comprises:

adjusting the appointment from the first channel to a second channel.

16. A system for scheduling appointments based on changing health conditions of users, comprising:

one or more processors; and one or more non-transitory computer-readable media storing processor-executable instructions which, when executed by the one or more processors, cause the one or more processors to perform operations comprising:

receiving, via one or more sensors at a first time, an initial health dataset of a user, wherein the initial health dataset indicates a health condition of the user;

applying a trained machine learning model to the initial health dataset to determine i) a second time to schedule an appointment for the user with a service provider, and ii) a frequency for monitoring a plurality of subsequent health datasets between the first time and the second time, wherein the trained machine learning model is configured to identify one or more other users with similar health profiles to the user and determine the second time and the frequency for monitoring based on the similar health profiles;

scheduling the appointment for the user at the second time;

receiving, via the one or more sensors after the first time and before the second time, the plurality of subsequent health datasets of the user, wherein the plurality of subsequent health datasets is received at an interval based on the frequency of monitoring;

determining at least one of health scores, rule scores, or medication scores for the user based on a processing of the plurality of subsequent health datasets;

determining a plurality of risk scores corresponding to the plurality of subsequent health datasets for the user based on the at least one of the health scores, the rule scores, or the medication scores, wherein the plurality of risk scores are compared to a risk score threshold to determine a risk associated with one or more health conditions of the user, including at least the health condition indicated by the initial health dataset, and wherein the risk associated with the one or more health conditions indicates a low-risk condition, a moderate-risk condition, a high-risk condition, a severe-risk condition, or a critical-risk condition;

determining a recent risk score, from among the plurality of risk scores for the user, has changed by a threshold level within a predefined time period, wherein the change in the recent risk score is indicative of a recent health condition trend of the user associated with a deterioration of the health condition indicated by the initial health dataset;

adjusting the scheduling of the appointment for the user from the second time to a third time, the third time being prior to the second time based on the risk associated with the recent risk score;

determining a treatment to respond to the deterioration of the health condition based on the initial health dataset and the plurality of subsequent health datasets; and transmitting a notification to a device associated with the user, the transmitting causing the device to display the notification about the adjusted scheduling of the appointment, wherein the determined treatment to respond to the deterioration of the health condition is administered to the user at the third time of the adjusted appointment.

17. One or more non-transitory computer-readable media for scheduling appointments based on changing health conditions of users, the one or more non-transitory computer-readable media storing processor-executable instructions which, when executed by one or more processors, cause the one or more processors to perform operations comprising:

receiving, via one or more sensors at a first time, an initial health dataset of a user, wherein the initial health dataset indicates a health condition of the user;

applying a trained machine learning model to the initial health dataset to determine i) a second time to schedule an appointment for the user with a service provider, and ii) a frequency for monitoring a plurality of subsequent health datasets between the first time and the second time, wherein the trained machine learning model is configured to identify one or more other users with similar health profiles to the user and determine the second time and the frequency for monitoring based on the similar health profiles;

scheduling the appointment for the user at the second time;

receiving, via the one or more sensors after the first time and before the second time, the plurality of subsequent health datasets of the user, wherein the plurality of subsequent health datasets is received at an interval based on the frequency of monitoring;

determining at least one of health scores, rule scores, or medication scores for the user based on a processing of the plurality of subsequent health datasets;

determining a plurality of risk scores corresponding to the plurality of subsequent health datasets for the user based on the at least one of the health scores, the rule scores, or the medication scores, wherein the plurality of risk scores are compared to a risk score threshold to determine a risk associated with one or more health conditions of the user, including at least the health condition indicated by the initial health dataset, and wherein the risk associated with the one or more health conditions indicates a low-risk condition, a moderate-risk condition, a high-risk condition, a severe-risk condition, or a critical-risk condition;

determining a recent risk score, from among the plurality of risk scores for the user, has changed by a threshold level within a predefined time period, wherein the change in the recent risk score is indicative of a recent health condition trend of the user associated with a deterioration of the health condition indicated by the initial health dataset;

adjusting the scheduling of the appointment for the user from the second time to a third time, the third time being prior to the second time based on the risk associated with the recent risk score;

determining a treatment to respond to the deterioration of the health condition based on the initial health dataset and the plurality of subsequent health datasets; and transmitting a notification to a device associated with the user, the transmitting causing the device to display the notification about the adjusted scheduling of the appointment, wherein the determined treatment to respond to the deterioration of the health condition is administered to the user at the third time of the adjusted appointment.

* * * * *